US012776123B2

(12) United States Patent
Cherubini et al.

(10) Patent No.: US 12,776,123 B2
(45) Date of Patent: Oct. 27, 2026

(54) COMPUTER-IMPLEMENTED SYSTEMS AND METHODS FOR INTELLIGENT IMAGE ANALYSIS USING SPATIO-TEMPORAL INFORMATION

(71) Applicant: COSMO ARTIFICIAL INTELLIGENCE—AI LIMITED, Dublin (IE)

(72) Inventors: Andrea Cherubini, Rome (IT); Nhan Ngo Dinh, Rome (IT); Pietro Salvagnini, Vigonza (IT); Carlo Biffi, Lecco (IT)

(73) Assignee: COSMO ARTIFICIAL INTELLIGENCE—AI LIMITED, Dublin (IE)

( * ) Notice: Subject to any disclaimer, the term of this patent is extended or adjusted under 35 U.S.C. 154(b) by 345 days.

(21) Appl. No.: 18/348,734

(22) Filed: Jul. 7, 2023

(65) Prior Publication Data

US 2024/0013383 A1 Jan. 11, 2024

Related U.S. Application Data

(60) Provisional application No. 63/368,025, filed on Jul. 8, 2022.

(30) Foreign Application Priority Data

Jul. 8, 2022 (EP) .................................... 22183987

(51) Int. Cl.
*G06V 10/62* (2022.01)
*A61B 1/00* (2006.01)
(Continued)

(52) U.S. Cl.
CPC ............ *G06V 10/62* (2022.01); *G06T 7/0002* (2013.01); *G06T 7/0012* (2013.01); *G06T 7/11* (2017.01);
(Continued)

(58) Field of Classification Search
CPC ...... G06V 10/62; G06V 10/443; G06V 20/44; G06V 20/47; G06T 7/11; G06T 7/73;
(Continued)

(56) References Cited

U.S. PATENT DOCUMENTS 10,586,306 B2 * 3/2020 Noh ..................... G06F 3/1423
2008/0031598 A1 2/2008 Ohara et al.
(Continued)

FOREIGN PATENT DOCUMENTS

WO 2020201772 A1 10/2020

OTHER PUBLICATIONS

E. Spyrou, D. Diamantis and D. K. Iakovidis, "Panoramic Visual Summaries for Efficient Reading of Capsule Endoscopy Videos," 2013 8th International Workshop on Semantic and Social Media Adaptation and Personalization, Bayonne, France, 2013, pp. 41-46 , doi: 10.1109/SMAP.2013.21. Dec. 12, 2013. (Year: 2013).*
(Continued)

*Primary Examiner* — Stephen R Koziol

(57) ABSTRACT

A computer-implemented method for detecting at least one feature of interest in images captured with an imaging device includes: receiving an ordered set of images and analyzing one or more subsets of the ordered set using a local spatio-temporal processing module. The local spatio-temporal processing module determines presence of characteristics related to the feature of interest in each image of each subset of images and annotates the subset of images. The method also includes processing a set of feature vectors of the ordered set of images using a global spatio-temporal processing module to refine the determined characteristics associated with each subset of images, and calculate one or more values for each image using a timeseries analysis module, the values being representative of the feature of interest and calculated using the refined characteristics associated with each subset of images and spatio-temporal information.

28 Claims, 20 Drawing Sheets

1000

(51) Int. Cl.

| | |
|---|---|
| ***G06T 7/00*** | (2017.01) |
| ***G06T 7/11*** | (2017.01) |
| ***G06T 7/73*** | (2017.01) |
| ***G06T 11/00*** | (2026.01) |
| ***G06V 10/44*** | (2022.01) |
| ***G06V 20/40*** | (2022.01) |
| ***G16H 15/00*** | (2018.01) |
| ***G16H 30/20*** | (2018.01) |
| ***G16H 30/40*** | (2018.01) |

(52) U.S. Cl.
CPC ................ *G06T 7/73* (2017.01); *G06T 11/00* (2013.01); *G06V 10/44* (2022.01); *G06V 10/443* (2022.01); *G06V 20/44* (2022.01); *G06V 20/47* (2022.01); *G16H 15/00* (2018.01); *G16H 30/20* (2018.01); *G16H 30/40* (2018.01); *A61B 1/000096* (2022.02); *G06T 2207/10016* (2013.01); *G06T 2207/10068* (2013.01); *G06T 2207/30028* (2013.01); *G06T 2207/30096* (2013.01); *G06T 2207/30168* (2013.01); *G06T 2210/41* (2013.01)

(58) Field of Classification Search
CPC ..... G06T 7/0002; G06T 7/0012; G06T 11/00; G06T 2207/10016; G16H 15/00; G16H 30/20; G16H 30/40; A61B 1/000096
See application file for complete search history.

(56) References Cited

U.S. PATENT DOCUMENTS

| | | | | |
|---|---|---|---|---|
| 2008/0165280 | A1 | 7/2008 | Deever et al. | |
| 2009/0041322 | A1 | 2/2009 | Wolf | |
| 2009/0092300 | A1 | 4/2009 | Jerebko et al. | |
| 2009/0244309 | A1 | 10/2009 | Maison et al. | |
| 2011/0301447 | A1* | 12/2011 | Park | A61B 1/000096 600/407 |
| 2013/0195422 | A1* | 8/2013 | Patil | H04N 21/6581 386/E5.028 |
| 2015/0254851 | A1 | 9/2015 | Daly et al. | |
| 2018/0301169 | A1* | 10/2018 | Ricciardi | G11B 27/036 |
| 2018/0315193 | A1 | 11/2018 | Paschalakis et al. | |
| 2019/0005334 | A1* | 1/2019 | Grundmann | G06V 10/771 |
| 2020/0066393 | A1 | 2/2020 | Kaiser et al. | |
| 2020/0273581 | A1 | 8/2020 | Wolf et al. | |
| 2021/0137368 | A1 | 5/2021 | Peleg | |
| 2022/0284927 | A1* | 9/2022 | Facer | G11B 27/031 |
| 2024/0013509 | A1 | 1/2024 | Cherubini et al. | |
| 2024/0020835 | A1 | 1/2024 | Cherubini et al. | |
| 2024/0046644 | A1* | 2/2024 | Liu | G06N 3/044 |

OTHER PUBLICATIONS

Adewole et al., Graph Convolutional Neural Network For Weakly Supervised Abnormality Localization In Long Capsule Endoscopy Videos, 2021 IEEE International Conference on Big Data (Big Data), IEEE, DOI: 10.1109/BIGDATA52589.2021.9671281, dated Dec. 15, 2021, 12 pages.
Biffi et al., A novel AI device for real-time optical characterization of colorectal polyps, NPJ Digital Medicine, vol. 5, No. 1, DOI: 10.1038/s41746-022-00633-6, https://www.nature.com/articles/s41746-022-00633-6.pdf, dated Jun. 30, 2022, 8 pages.
Extended European Search Report (EESR), EP Application No. 22183987.1, dated Mar. 10, 2023, 17 pages.
International Search Report and Written Opinion, PCT/EP2023/068921, dated Oct. 16, 2023, 28 pages.
International Search Report and Written Opinion, PCT/EP2023/068930, dated Oct. 16, 2023, 13 pages.
International Search Report and Written Opinion, PCT/EP2023/068935, dated Oct. 10, 2023, 15 pages.
Liedlgruber et al., Computer-Aided Decision Support Systems for Endoscopy in the Gastrointestinal Tract: A Review, IEEE Reviews in Biomedical Engineering, vol. 4, 73-88, DOI: 10.1109/RBME.2011.2175445, 2011, 16 pages.
Puyal et al., Endoscopic Polyp Segmentation Using a Hybrid 2D / 3D CNN, Topics in Cryptology—CR-RSA 2020: The Cryptographers' Track at the RSA Conference 2020, San Francisco, CA, USA, dated Feb. 24-28, 2020, 11 pages.
Yu et al., Integrating Online and Offline Three-Dimensional Deep Learning for Automated Polyp Detection in Colonoscopy Videos, IEEE Journal of Biomedical and Health Informatics, IEEE, Piscataway, NJ, USA, vol. 21, No. 1, ISSN: 2168-2194, DOI: 10.1109/JBHI.2016.2637004, dated Jan. 1, 2017, 11 pages.

* cited by examiner

690

1000

COMPUTER-IMPLEMENTED SYSTEMS AND METHODS FOR INTELLIGENT IMAGE ANALYSIS USING SPATIO-TEMPORAL INFORMATION

TECHNICAL FIELD

The present disclosure relates generally to the field of video processing and image analysis. More specifically, and without limitation, this disclosure relates to systems, methods, and computer-readable media for processing captured video content from an imaging device and performing intelligent image analysis, such as determining the presence of one or more features of interest or actions taken during a medical procedure. The systems and methods disclosed herein may be used in various applications, including for medical image analysis and diagnosis.

BACKGROUND

In video processing and image analysis systems, it is often desirable to detect objects or features of interest. A feature of interest may be a person, place, or thing. In some applications, such as systems and methods for medical image analysis, the location and classification of a detected feature of interest (e.g., an abnormality such as a formation on or of human tissue) is important for diagnosis of a patient. However, extant computer-implemented systems and methods suffer from a number of drawbacks, including the inability to accurately detect features of interest and/or recognize characteristics related to features of interest. In addition, extant systems and methods are inefficient and do not provide ways to analyze images intelligently, including with regard to the image sequence or presence of events.

Modern medical procedures require precise and accurate examination of a patient's body and organs. Endoscopy is a medical procedure aimed at providing a physician with video images of the internal parts of a patient's body and organs for diagnosis. In the gastrointestinal tract of the human body, the procedure can be performed by introducing a probe with a video camera through the mouth or anus of the patient. During an endoscopic procedure, a physician navigates manually the probe through the gastrointestinal tract while watching in real-time the video on a display device. The video may also be captured, stored, and examined after the endoscopic procedure. As an alternative, capsule endoscopy is a procedure where a capsule containing a small camera is swallowed to examine the gastrointestinal tract of a patient. The sequence of images taken by the capsule during its transit are transmitted wirelessly to a receiving device and stored for examination by the physician after completion of the procedure. The frame rate of capsule device can vary (e.g., 2 to 6 frames per second) and a large volume of images may be taken during an examination procedure.

From a computer vision perspective, the captured content from either a real-time video endoscopy or capsule procedure is a temporally ordered succession of images containing information about a patient, e.g., the internal mucosa of the gastrointestinal tract. Accurate and precise analysis of the captured image data is essential to properly examine the patient and identify lesions, polyps, or other features of interest. Also, there is usually a large number of images collected for each patient. One of the most important medical tasks that needs to be performed by the physician is the examination of this large set of images to make a proper diagnosis including with respect to the presence or absence of features of interest, such as pathological regions in the imaged mucosa. However, going through these images manually is time consuming and inefficient. As a result, the review process can lead to a physician making errors and/or making a misdiagnosis.

In order to improve diagnosis, decrease the time needed for medical image examination, and reduce the possibility of errors, the inventors have determined that it is desirable to have a computer-implemented system and method that is able to intelligently process images and identify the presence of a pathology or other features of interest within all images from a video endoscopy or capsule procedure, or other medical procedure. By way of example, a feature of interest may also include an action being taken on or in the images, an anatomical location or other location of interest in the images, a clinical index level of the images, and so on. Trained neural networks, spatio-temporal image analysis, and other features and techniques are disclosed herein for this purpose. As will be appreciated from this disclosure, the present invention and embodiments may be applied to a wide variety of image capture and analysis applications and are not limited to the examples presented herein.

SUMMARY

Embodiments of the present disclosure include systems, methods, and computer-readable media for processing images captured from an imaging device and performing an intelligent image analysis, such as determining the presence of one or more features of interest. Systems and methods consistent with the present disclosure can provide benefits over extant systems and techniques, including by addressing one more of the above-referenced drawbacks and/or other shortcomings of extant systems and techniques. Consistent with some disclosed embodiments, systems, methods, and computer-readable media are provided for processing images from a video endoscopy or capsule procedure or other medical procedure, where the images are temporally ordered. Example embodiments include systems and methods that intelligently process captured images using spatio-temporal information to accurately assess the likelihood of the presence of an abnormality, a pathology, or other features of interest within the images. As a further example, a feature of interest can be a parameter or statistic related to an endoscopy or capsule procedure or other medical procedure. By way of example, a feature of interest of an endoscopy procedure may be a clean withdrawal time or time for traversal of a probe or a capsule through an organ. A feature of interest in an image may also be determined based on the presence or absence of characteristics related to that feature of interest. These and other embodiments, features, and implementations are described more fully herein. A feature of interest may be any feature in or related to one or more image, in particular in or related to a scene or field of view represented in one or more image, that is identifiable, or detectable, by analyzing the or each image. A feature of interest may for example be an object, or a location, or an action or a condition (e.g. a clinical index level).

In some embodiments, images captured by an imaging device, such as an endoscopy video camera or capsule camera, include images of a gastrointestinal tract or organ. The images may come from a medical imaging device used during, for example, a gastroscopy, a colonoscopy, or an enteroscopy. A feature of interest in the images may be an abnormality or other pathology, for example. The abnormality or pathology may comprise a formation on or of human tissue, a change in human tissue from one type of cell to another type of cell, an absence of human tissue from a location where the human tissue is expected, or a formation on or of human tissue. The formation may comprise a lesion, a polypoid lesion, or a non-polypoid lesion. Other examples of features of interest include an anatomical or other location, an action, a clinical index (e.g., cleanliness), and so on. Consequently, as will be appreciated from this disclosure, the example embodiments may be utilized in a medical context in a manner that is not specific to any single disease but may rather be generally applied.

According to one general aspect of the present disclosure, a computer-implemented system is provided for processing images captured by an imaging device. The computer-implemented system may include at least one processor configured to detect at least one feature of interest in images captured by an imaging device. The at least one processor may be configured to: receive an ordered set of images from the captured images, the ordered set of images being temporally ordered; analyze one or more subsets of the ordered set of images individually using a local spatio-temporal processing module, the local spatio-temporal processing module being configured to determine the presence of characteristics related to at least one feature of interest in each image of each subset of images and to annotate the subset images with a feature vector based on the determined characteristics in each image of each subset of images; process a set of feature vectors of the ordered set of images using a global spatio-temporal processing module, the global spatio-temporal processing module being configured to refine the determined characteristics associated with each subset of images, wherein each feature vector of the set of feature vectors includes information about each determined characteristic of the at least one feature of interest; and calculate a numerical value for each image using a time-series analysis module, the numerical value being representative of the presence of at least one feature of interest and calculated using the refined characteristics associated each subset of images and spatio-temporal information. Further, the at least one processor may be configured to generate a report on the at least one feature of interest using the numerical value associated with each image of each subset of the ordered set of images. The report may be generated after the completion of the endoscopy or other medical procedure. The report may include information related to all features of interest identified in the processed images.

The at least one processor of the computer-implemented system may be further configured to determine a likelihood of characteristics related to at least one feature of interest in each image of the subset of images. Additionally, the at least one processor may be configured to determine the likelihood of characteristics in each image of the subset of images by encoding each image of the subset of the images and aggregating the spatio-temporal information of the determined characteristics using a recurrent neural network or a temporal convolution network.

To refine the determined characteristics, a non-causal temporal convolution network may be utilized. For example, the at least one processor of the system may be configured to refine the likelihood of the characteristics in each image of the subset of images by applying a non-causal temporal convolution network. The at least one processor may be further configured to refine the likelihood of the characteristics by applying one or more signal processing techniques including low pass filtering and/or Gaussian smoothing, for example.

According to a still further aspect, the at least one processor of the system may be configured to analyze the ordered set of images using the local spatio-temporal processing module to determine presence of characteristics by determining a vector of quality scores, wherein each quality score in the vector of quality scores corresponds to each image of the subset of the images. Additionally, the at least one processor may be configured to process ordered set of images using the global spatio-temporal processing module by refining quality scores of each image of the subset of images of the one or more subsets of the ordered set of images using signal processing techniques. The at least one processor may be further configured to analyze the one or more subsets of the ordered set of images using the local spatio-temporal processing module to determine the presence of characteristics by generating, using a deep convolutional neural network, a pixel-wise binary mask for each image of the subset of images. The at least one processor may be further configured to process the one or more subsets of the ordered set of images using the global spatio-temporal processing module by refining the binary mask for image segmentation using morphological operations exploiting prior information about the shape and distribution of the determined characteristics.

As disclosed herein, implementations may include one or more of the following features. The determined likelihood of characteristics in each image of the subset of images may include a float value between 0 and 1. The quality score may be an ordinal number between 0 and R, wherein a score 0 represents minimum quality and a score R represents the maximum quality. The numerical value may be associated with each image is interpretable to determine the probability to identify the at least one feature of interest within the image. The output may be a first numerical value for an image where the at least one feature of interest is not detected. The output may be a second numerical value for an image where the at least one feature of interest is detected. The size or volume of the subset of images may be configurable by a user of the system. The size or volume of the subset of images may be dynamically determined based on a requested feature of interest. The size or volume of the subset of images may be dynamically determined based on the determined characteristics. The one or more subsets of images may include shared images.

Another general aspect of the present disclosure related to a computer-implemented system for spatio-temporal analysis of images captured with an imaging device. The computer-implemented system may comprise at least one processor configured to receive video captured from an imaging device including a plurality of image frames. The at least one processor may be further configured to: access a temporally ordered set of images from the captured images; detect, using an event detector module, an occurrence of an event in the temporally ordered set of images, wherein a start time and an end time of the event are identified by a start image frame and an end image frame in the temporally ordered set of images; select, using a frame selector module, an image from a group of images in the temporally ordered set of images, bounded by the start image frame and the end image frame, based on an associated score and a quality score of the image, wherein the associated score of the selected image indicates a presence of at least one feature of interest; merge a subset of images from the selected images based on a matching presence of the at least one feature of interest using an objects descriptor module, wherein the subset of images is identified based on spatial and temporal coherence using spatio-temporal information; and split the temporally ordered set of images in temporal intervals which satisfy the temporal coherence of a selected task.

According to the disclosed system, the at least one processor may be further configured to determine spatio-temporal information of characteristics related to the at least one feature of interest for subsets of images of the video content using a local spatio-temporal processing module and determine the spatio-temporal information of all images of the video content using a global spatio-temporal processing module. In addition, the at least one processor may be configured to split the temporally ordered set of images in temporal intervals by identifying a subset of temporally ordered set of images with the presence of the at least one feature of interest. The at least one processor may also be configured to identify a subset of temporally ordered set of images with the presence of the at least one future of interest by adding bookmarks to images in the temporally ordered set of images, wherein the bookmarked images are part of the subset of temporally ordered set of images. Additionally, or alternatively, the at least one processor may be configured to identify a subset of temporally ordered set of images with the presence of the at least one feature of interest by extracting a set of images from the subset of the temporally ordered set of images.

Implementations may include one or more of the following features. The extracted set of images may include characteristics related to the at least one feature of interest. The color may vary with a level of relevance of an image of the subset of temporally ordered set of images for the at least one feature of interest. The color may vary with a level of relevance of an image of the subset of temporally ordered set of images for characteristics related to the at least one feature of interest.

Another general aspect includes a computer-implemented system for performing a plurality of tasks on a set of images. The computer-implemented system may comprise at least one processor configured to receive video captured from an imaging device including a set of image frames. The at least one processor may be further configured to: receive a plurality of tasks, wherein at least one task of the plurality of tasks is associated with a request to identify at least one feature of interest in the set of images; analyze, using a local spatio-temporal processing module, a subset of images of the set of images to identify the presence of characteristics associated with the at least one feature of interest; and iterate execution of a timeseries analysis module for each task of the plurality of tasks to associate a numerical score for each task with each image of the set of images.

Consistent with the present disclosure, a system of one or more computers can be configured to perform operations or actions by virtue of having software, firmware, hardware, or a combination of them installed for the system that in operation causes or cause the system to perform those operations or actions. One or more computer programs can be configured to perform operations or actions by virtue of including instructions that, when executed by data processing apparatus (such as one or more processors), cause the apparatus to perform such operations or actions.

Systems and methods consistent with the present disclosure may be implemented using any suitable combination of software, firmware, and hardware. Implementations of the present disclosure may include programs or instructions that are machine constructed and/or programmed specifically for performing functions associated with the disclosed operations or actions. Still further, non-transitory computer-readable storage media may be used that store program instructions, which are executable by at least one processor to perform the steps and/or methods described herein.

It will be understood that the foregoing general description and the following detailed description are exemplary and explanatory only and are not restrictive of the disclosed embodiments.

BRIEF DESCRIPTION OF THE DRAWINGS

The following drawings which comprise a part of this specification, illustrate several embodiments of the present disclosure and, together with the description, serve to explain the principles and features of the disclosed embodiments.

In the Drawings.

DETAILED DESCRIPTION

Figure 1A:
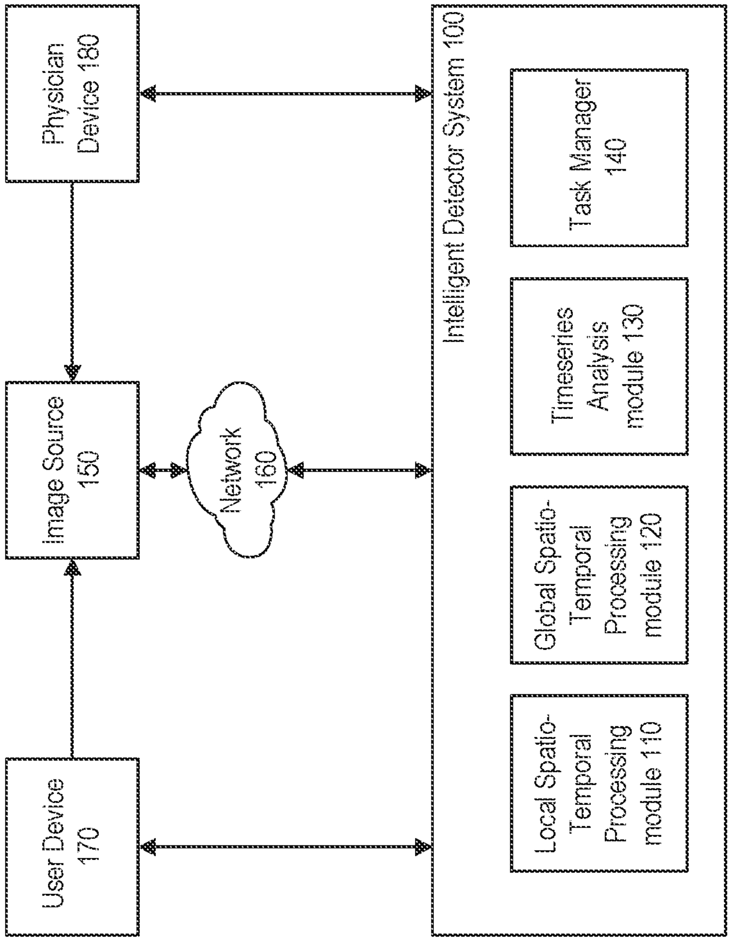
FIG. 1A is a block diagram of an example intelligent detector system, consistent with embodiments of the present disclosure.

Example embodiments are described below with reference to the accompanying drawings. The figures are not necessarily drawn to scale. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It should also be noted that as used herein and in the appended claims, the singular forms "a," "an," and "the" include plural references unless the context clearly dictates otherwise.

In the following description, various working examples are provided for illustrative purposes. However, it will be appreciated that the present disclosure may be practiced without one or more of these details.

Throughout this disclosure there are references to "disclosed embodiments," which refer to examples of inventive ideas, concepts, and/or manifestations described herein. Many related and unrelated embodiments are described throughout this disclosure. The fact that some "disclosed embodiments" are described as exhibiting a feature or characteristic does not mean that other disclosed embodiments necessarily share that feature or characteristic.

Embodiments described herein include non-transitory computer readable medium containing instructions that when executed by at least one processor, cause the at least one processor to perform a method or set of operations. Non-transitory computer readable mediums may be any medium capable of storing data in any memory in a way that may be read by any computing device with a processor to carry out methods or any other instructions stored in the memory. The non-transitory computer readable medium may be implemented as software, firmware, hardware, or any combination thereof. Software may preferably be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine may be implemented on a computer platform having hardware such as one or more central processing units ("CPUs"), a memory, and input/output interfaces. The computer platform may also include an operating system and microinstruction code. The various processes and functions described in this disclosure may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium may be any computer readable medium except for a transitory propagating signal.

The memory may include any mechanism for storing electronic data or instructions, including Random Access Memory (RAM), a Read-Only Memory (ROM), a hard disk, an optical disk, a magnetic medium, a flash memory, other permanent, fixed, volatile or non-volatile memory. The memory may include one or more separate storage devices collocated or disbursed, capable of storing data structures, instructions, or any other data. The memory may further include a memory portion containing instructions for the processor to execute. The memory may also be used as a working memory device for the processors or as a temporary storage.

Some embodiments may involve at least one processor. A processor may be any physical device or group of devices having electric circuitry that performs a logic operation on input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory.

In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically, or by other means that permit them to interact.

Embodiments consistent with the present disclosure may involve a network. A network may constitute any type of physical or wireless computer networking arrangement used to exchange data. For example, a network may be the Internet, a private data network, a virtual private network using a public network, a Wi-Fi network, a LAN or WAN network, and/or other suitable connections that may enable information exchange among various components of the system. In some embodiments, a network may include one or more physical links used to exchange data, such as Ethernet, coaxial cables, twisted pair cables, fiber optics, or any other suitable physical medium for exchanging data. A network may also include one or more networks, such as a private network, a public switched telephone network ("PSTN"), the Internet, and/or a wireless cellular network. A network may be a secured network or unsecured network. In other embodiments, one or more components of the system may communicate directly through a dedicated communication network. Direct communications may use any suitable technologies, including, for example, BLUETOOTH™, BLUETOOTH LE™ (BLE), Wi-Fi, near field communications (NFC), or other suitable communication methods that provide a medium for exchanging data and/or information between separate entities.

In some embodiments, machine learning networks or algorithms may be trained using training examples, for example in the cases described below. Some non-limiting examples of such machine learning algorithms may include classification algorithms, video classification algorithms, data regressions algorithms, image segmentation algorithms, temporal video segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, action recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning network or algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. The training may be supervised or non-supervised, or a combination thereof. In some examples, engineers, scientists, processes, and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by a process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters. The machine learning networks or algorithms may be further retrained based on any output.

Certain embodiments disclosed herein may include computer-implemented systems for performing operations or methods comprising a series of steps. The computer-implemented systems and methods may be implemented by one or more computing devices, which may include one or more processors as described herein, configured to process real-time video. The computing device may be one or more computers or any other devices capable of processing data. Such computing devices may include a display such as an LCD display, augmented reality (AR), or virtual reality (VR) display. However, the computing device may also be implemented in a computing system that includes a back end component (e.g., as a data server), or that includes a middleware component (e.g., an application server), or that includes a front end component (e.g., a user device having a graphical user interface or a Web browser through which a user can interact with an implementation of the systems and techniques described here), or any combination of such back end, middleware, or front end components. The components of the system and/or the computing device can be interconnected by any form or medium of digital data communication (e.g., a communication network). Examples of communication networks include a local area network ("LAN"), a wide area network ("WAN"), and the Internet. The computing device can include clients and servers. A client and server are generally remote from each other and typically interact through a communication network. The relationship between client and server arises by virtue of computer programs running on the respective computers and having a client-server relationship with each other.

FIG. 1A is a block diagram of an example intelligent detector system 100, consistent with embodiments of the present disclosure. As further disclosed herein, intelligent detector system 100 may be a computer-implemented system and comprise of one or more convolutional neural networks (CNN) to process images from a medical procedure to identify requested features of interest in the images. Feature(s) of interest can be a pathology or a list of pathologies a physician is looking for in the images (e.g., to diagnosis a patient). By way of further example, a feature of interest may also include an action to be taken on or in the images, an anatomical location or other location of interest in the images, a clinical index level of the images, and so on. These and other examples are within the scope of the present disclosure. By way of example, an action may include actions taken by a physician during the medical procedure or as part of a subsequent procedure, including actions or procedures identified by system 100 as a result of a spatio-temporal review of images from the medical procedure. For example, an action may include a recommended action or procedure in accordance with a medical guideline, such as performing a biopsy, removing a lesion, or exploring/analyzing a surface/mucosa of an organ. The action or procedure may be identified based on the images captured and processed by intelligent detector system 100.

Intelligent detector system 100 may receive as input a collection of temporally ordered images of a medical procedure, such as an endoscopy or colonoscopy procedure. Intelligent detector system 100 may output a report or information including one or more numerical value(s) (e.g., score(s)) for each image. The numerical value(s) may relate to a medical category such as a particular pathology and provide information regarding the probability of the presence of the medical category within an image frame. The images processed by intelligent detector system 100 may be images captured from a medical procedure that are stored in a database or memory device for subsequent retrieval and processing by intelligent detector system 100. In some embodiments, the output provided by intelligent detector system 100 resulting from processing the images may include a report with numerical score(s) assigned to the images and recommended next steps in accordance with medical guideline(s), for example. The report may be generated after the completion of the endoscopy or other medical procedure. The report may include information related to all features of interest identified in the processed images. Still further, in some embodiments, the output provided by intelligent detector system 100 may include recommended action(s) to be performed by the physician (e.g., performing a biopsy, removing a lesion, exploring/analyzing the surface/mucosa of an organ, etc.) in view of an identified feature(s) of interest in the images from the medical procedure. During a medical procedure, intelligent detector system 100 may directly receive the video or image frames from a medical image device, process the video or images frames, and provide during the procedure or right after the medical procedure (i.e. a short time interval, from no time to a few minutes) as feedback to the operator regarding performed action(s) by the operator, as well as a final report containing multiple measured variables, clinical indices and details about what was observed and/or in which anatomical location and/or how the operator behaved/acted during the medical procedure. Performed actions may include a recommended action or procedure in accordance with a medical guideline, such as performing a biopsy, removing a lesion, or exploring/analyzing a surface/mucosa of an organ. In some embodiments, a recommended action may be part of a set of recommended actions based on medical guidelines. A detailed description of an example computer system implementing intelligent detector system 100 for real-time processing is presented in FIG. 1B description below.

As disclosed herein, intelligent detector system 100 may generate a report after completion of a medical procedure that includes information based on the processing of the captured video by local spatio-temporal processing module 110, global spatio-temporal processing module 120, and time series analysis module 130. The report may include information related to the features of interest identified during the medical procedure, as well as other information such as numerical value(s) or score(s) for each image. As explained, the numerical value(s) may relate to a medical category such as a particular pathology and provide information regarding the probability of the presence of the medical category within an image frame. Further details regarding intelligent detector system 100 and the operations of local spatio-temporal processing module 110, global spatio-temporal processing module 120, and timeseries analysis module 130 are provided below with reference to the attached drawings.

In some embodiments, the report generated by system 100 may include additional recommended action(s) based on the processing of stored images from a medical procedure or real-time processing of images from the medical procedure. Additional recommended action(s) could include actions or procedures that could have been performed during a medical procedure and actions or procedures to be performed after the medical procedure. Additional recommended action(s) may be part of a set of recommended action(s) based on medical guidelines. Further, as described above, system 100 may process video in real-time to provide concurrent feedback to an operator about what is happening or identified in the video and during a medical procedure.

Figure 10:
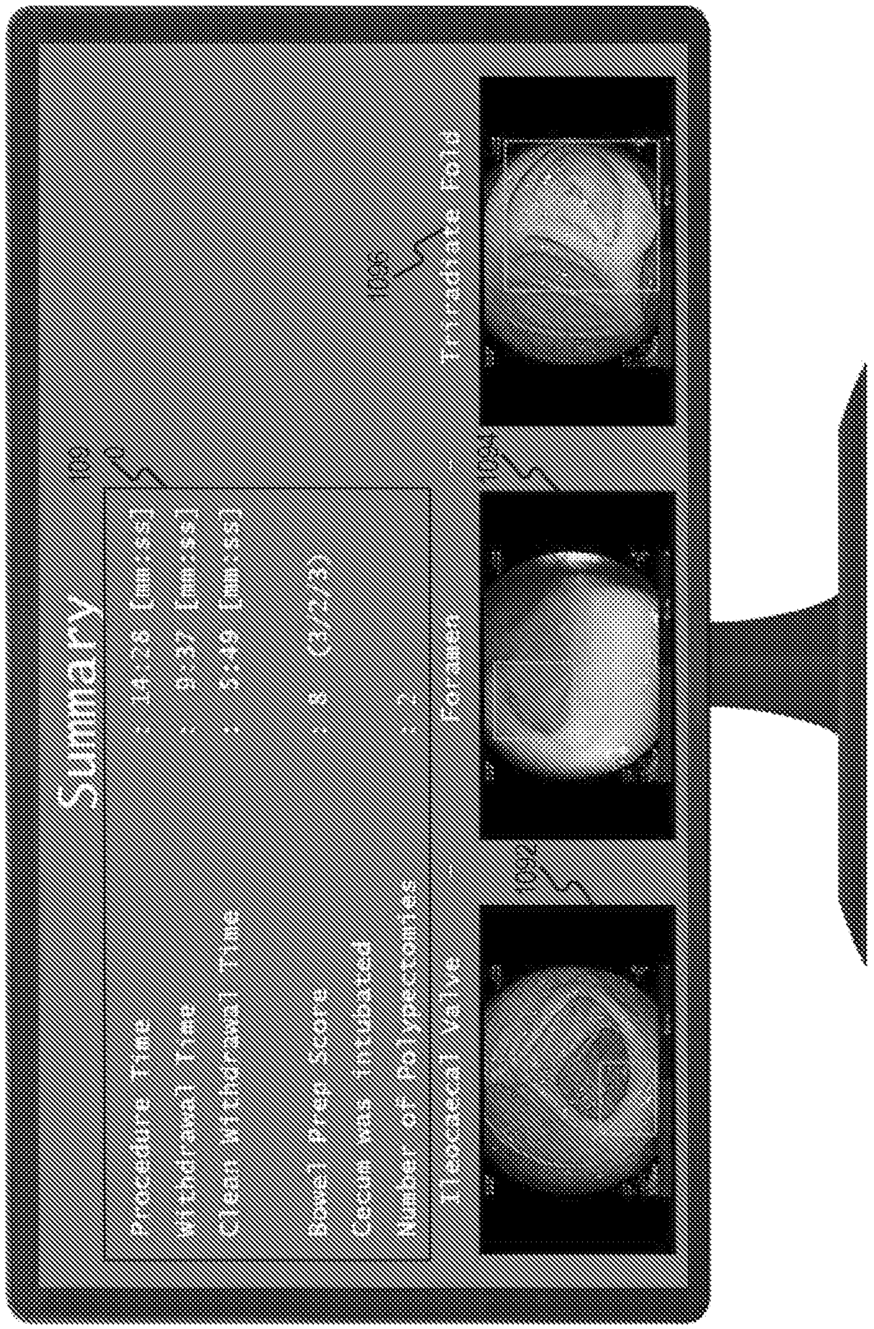
FIG. 10 illustrates an example dashboard with output summaries generated using an example intelligent detector system, consistent with embodiments of the present disclosure.

The output generated by intelligent detector system 100 may include a dashboard display or similar report (see, e.g., FIG. 10). The dashboard may provide a summary report of the medical procedure, for example, an endoscopy or colonoscopy. The dashboard may provide quality scores and/or other information for the procedure. The scores and/or other information may summarize the examination behavior of the healthcare professional and provide information for identified features of interest, such as the number of identified polyps. In some embodiments, the information generated by system 100 is provided and displayed as an overlay on the video from the medical procedure and thus an operator can view the information as part of an augmented video feed during or right after the end of the medical procedure. This information may be provided with some or no delay.

Intelligent detector system 100 may also generate reports in the form of an electronic file, a set of data, or data transmission. By way of example, the output generated by system 100 may follow a standardized format and/or be integrated into records such as electronic health records (EHR). The output of system 100 may also be compliant with regulations such as HIPAA for interoperability and privacy. In some embodiments, the output may be integrated into other reports. For example, the output of intelligent detector system 100 may be integrated into an electronic medical or health record for a patient. Intelligent detector system 100 may include an API to facilitate such integration and/or provide output in the form of a standardized data set or template. Standardized templates may include predefined forms or tables that can be filled with data values generated by intelligent detector system 100 by processing input video or image frames from a medical procedure. In some embodiments, reports may be generated by system 100 in a machine-readable format, such as an XML file, to support their transmission or storage, as well as integration with other systems and applications. In some embodiments, reports may be provided in other formats such as a Word, Excel, HTML, or PDF file format. In some embodiments, intelligent detector system 100 may upload data or a report to a server or database over a network (see, e.g., network 160 in FIG. 1A). Intelligent detector system 100 may also transfer to a server or database by making an API call and transmitting output data or a formatted report, for example, as a JSON document.

FIG. 10 illustrates an example dashboard 1000 with an output summary 1090 generated using an intelligent detector system (such as intelligent detector system 100), consistent with embodiments of the present disclosure. Using the modules of intelligent detector system 100, output summary 1090 may be generated for the procedure. Output summary 1090 may provide quality scores and/or other information such as the procedure time, the withdrawal time, and the clean withdrawal time. Further examples of information that may be part of summary 1090 include the time spent performing specific actions (such as recommended action(s) discussed above) and the time spent in distinct anatomical locations. Information related to features of interest, such as polyps, may also be provided. For example, timeseries analysis module 130 may generate a summary of number of polyps identified based on characteristics observed in the image frames. Timeseries analysis module 130 may aggregate the information generated by processing images of input video using local and global spatio-temporal processing modules 110 and 120. Summary dashboard 1000 may also include visual descriptions of features of interest identified by intelligent detector system 100. For example, selected frames of video of a procedure may be augmented with markings such as green bounding box about the location of each identified feature of interest, as shown in frames 1092, 1094, and 1096. The frames may be related to different examined portions of the colon, such as the ileocecal valve, foramen, and triradiate fold, which themselves may be features of interest requested by a user of intelligent detector system 100. Although the example of FIG. 10 illustrates the information for a procedure being displayed as part of a single dashboard, multiple dashboards may be generated with output summaries for each of portion of the colon or other organ examined as part of the medical procedure. In some embodiments, combined scores or values are generated based on inputs received as multiple vectors (e.g., image score vectors) generated by local and global spatio-temporal processing modules 110 and 120.

As disclosed above, a feature of interest may relate to a medical category or pathology. Intelligent detector system 100 may be implemented to handle a request to detect one or more medical categories (i.e., one or more features of interest) in the images. In the case of multiple features of interest, one instance of the components of intelligent detector system 100 may be implemented for each medical category or feature of interest. As will be appreciated from this disclosure, instances of intelligent detector system 100 may be implemented with any combination of hardware, firmware, and software, according to the speed or throughput needs, volume of images to be processed, and other requirements of the system.

In some embodiments, a single instance of intelligent detector system 100 may output multiple numerical values for each image, one for each medical category. In one example embodiment, pathologies detected by intelligent detector system 100 may include detecting polyps in the colon mucosa. Further, by way of example, intelligent detector system 100 may output a numerical value (e.g., 0) for all images among the input images where a polyp is not detected by intelligent detector system 100 and may output another numerical value (e.g., 1) for all images among the input images where the intelligent detector detects at least one polyp. In some embodiments, the numerical values can be arranged relative to a range or scale and/or indicate the probability of the presence of a polyp or other feature of interest.

The source of the input images may vary according to the imaging device, memory device, and/or needs of the application. For example, intelligent detector system 100 may be configured to process a video feed directly from a video endoscopy device and receive temporally ordered input images that are subsequently processed by the system, consistent with the embodiments disclosed herein. As a further example, intelligent detector system 100 may be configured to receive the input images from a database or memory device, the stored images being temporally ordered and previously captured using an imaging device, such as a video camera of an endoscopy device or a camera of a capsule device. Images received by intelligent detector system 100 may be processed and analyzed to identify one or more features of interest, such as one or more types of polyps or lesions.

The example system of FIG. 1A may be implemented in various environments and for various applications. For example, the captured input images may be stored in a local database or memory device or they be accessed and received by intelligent detector system 100 over a network from a remote storage location, such as cloud storage. Intelligent detector system 100 may also be configured to process a streaming video feed from a current medical procedure and to process the input images are they are collected from the feed (e.g., via pre-processing and buffering). Further, the operation of intelligent detector system 100 may be programmed or triggered to start upon one or more conditions. For example, intelligent detector system 100 may be configured to analyze input images directly upon receiving it (e.g., via a video feed or a set of stored input images from memory) or upon receiving commands from a user. The output of intelligent detector system 100 may also be configured as desired. For example, as previously discussed, intelligent detector system 100 may analyze input images for one or more features of interest and generate a report indicating the presence of the one or more features of interest in the processed images. The report may take the form of an electronic file, a graphical display, and/or electronic transmission of data. As will be appreciated, other outputs and report formats are within the scope of the present disclosure. In some embodiments, reports of different formats may be preconfigured and used as templates for generating reports by filling the template with values generated by intelligent detector system 100. In some embodiments, reports are formatted to be integrated into other reporting systems, such as electronic medical records (EMRs). The report format may be a machine-readable format such as XML or Excel for integrating with other reporting systems.

By way of example, intelligent detector system 100 may process a recorded video or images and provide a fully automated report and/or other output that details the feature(s) of interest observed in the processed images. Intelligent detector system 100 may use artificial intelligence or machine learning components to efficiently and accurately process the input images and make decision about the presence of features of interest based on image analysis and/or spatio-temporal information. Further, for each feature of interest that is requested or under investigation, intelligent detector system 100 can estimate its presence within the images and provide a report or other output with information indicating the likelihood of the presence of that feature and other details, such as the relative time from the beginning of the procedure or sequence of images where the feature of interest appears, estimated anatomical location, duration, most significant images, location within these images, and/or number of occurrences.

In one embodiment, intelligent detector system 100 may be configured to automatically determine the presence of gastrointestinal pathologies without the aid of a physician. As discussed above, the input images may be captured and received in different ways and using different types of imaging devices. For example, a video endoscopy device or capsule device or other medical device or other imaging device may record and provide the input images. The input images may be part of a live video feed or may be part of stored set of images received from a local or remote storage location (e.g., a local database or cloud storage). Intelligent detector system 100 may be operated as part of a procedure or service at a clinic or hospital, or it may be provided as an online or cloud service for end users to enable self-diagnostics or remote testing.

By way of example, to start an examination procedure, a user may ingest a capsule device or pill cam. The capsule device may include an imaging device and during the procedure wirelessly transmit images of the user's gastrointestinal tract to a smartphone, tablet, laptop, computer, or other device (e.g., user device 170). The captured images may then be uploaded by a network connection to a database, cloud storage or other storage device (e.g., image source 150). Intelligent detector system 100 may receive the input images from the image source and analyze the images for one or more requested feature(s) of interest (e.g., polyps or lesions). A final report may then be electronically provided as output to the user and/or their physician. The report may include a scoring or probability indicator for each observed feature of interest and/or other relevant information or medical recommendations. Additionally, intelligent detector system 100 can detect pathophysiological characteristics that are related to and an indicator of a feature of interest and score those characteristics that are determined to be present. Examples of such characteristics include bleeding, inflammation, ulceration, neoplastic tissues, etc. Further, in response to detected feature(s) of interest, the report may include information or recommendations based on medical guidelines, such as recommendations to consult with a physician and/or to take additional diagnostic examinations, for example. One or more actions may also be recommended to the physician (e.g., perform a biopsy, remove a lesion, explore/analyze the surface/mucosa of an organ, etc.) based on the analysis of the images by intelligent detector system 100 either in real-time with the medical procedure or after the medical procedure is completed.

As another example, intelligent detector system 100 could assist a physician or specialist with analyzing the video content recorded during a medical procedure or examination. The captured images may be part of the video content recorded during, for example, a gastroscopy, a colonoscopy, or an enteroscopy procedure. Based on the analysis performed by intelligent detector system 100, the full video recording could be displayed to the physician or specialist along with a colored timeline bar, where different colors correspond to different feature(s) of interest and/or scores for the identified feature(s) of interest.

As a still further example, a physician, specialist, or other individual could use intelligent detector system 100 to create a synopsis of the video recording or set of images by focusing on images with the desired feature(s) of interest and discarding irrelevant image frames. Intelligent detector system 100 may be configured to allow a physician or user to tune or select the feature(s) of interest for detection and the duration of each synopsis based on a total duration time and/or other parameters, such as preset preceding and trailing times before and after a sequence of frames with the selected feature(s) of interest. Intelligent detector system 100 can also be configured to combine all or the most relevant frames according to the requested feature(s) of interest.

As illustrated in FIG. 1A, intelligent detector system 100 may include a local spatio-temporal processing module 110, a global spatio-temporal processing module 120, a time-series analysis module 130, and a task manager 140. These components may be implemented through any suitable combination of hardware, software, and/or firmware. Further, the number and arrangement of these components may be modified and it will be appreciated that the example embodiment of FIG. 1A is provided for purposes for illustration and does not limited the scope of the invention and its embodiments. Further example features and details related to these components is provided below, including with respect to FIG. 1B and FIGS. 3A-3C.

Referring again to the example embodiment of FIG. 1A, local spatio-temporal processing module 110 may be configured to provide a local perspective by processing subset(s) of images of an input video or set of input images. Local spatio-temporal processing module 110 may select subset(s) of images and process the images to generate scores based on the determined presence of characteristics related to one or more features of interest. For example, assume an endoscopy input video V includes a collection of T image frames. Characteristics may define the features of interest requested by a user of intelligent detector system 100. For example, characteristics may include physical and/or biological aspects, such as size, orientation, color, shape, etc. of a feature of interest. Characteristics may also include metadata such as data identifying a portion of a video or time period in a video. For example, characteristics of a colonoscopy procedure video may identify portion(s) of the colon, such as ascending, transverse, or descending. In another example, characteristics may relate to one or more portions of an endoscopy procedure video, such as the amount of motion in the images, the presence of an instrument, or the duration of a segment with reduced motion. Characteristics defining content may also indicate the behavior of a physician, clinician, or other individual performing a medical procedure. For example, portions of the video with the longest pauses with no movement or greatest time exploring the surface of an organ. In some embodiments, characteristics may be a feature of interest. For instance, features of interest and characteristics of a colonoscopy procedure video may be a portion of colon, such as ascending, transverse, or descending.

Local spatio-temporal processing module 110 may be configured to process the whole input video in chunks by iterating over sequential batches or subsets of N image frames. Local spatio-temporal processing module 110 may also be configured to provide output that includes vectors or quality scores representing the determined characteristics of the feature(s) of interest in each image frame. In some embodiments, local spatio-temporal processing module 110 may output quality values and segmentation maps associated with each image frame. Further example details related to local spatio-temporal processing module 110 are provided below with reference to the FIG. 3A embodiment.

The subset of images processed by local spatio-temporal processing module 110 may include shared or overlapping images. Further, the size or arrangement of the subset of images may be defined or controlled based on one or more factors. For example, the size or volume of the subset of images may be configurable by a physician or other user of the system. As a further example, local spatio-temporal processing module 110 may be configured so that the size or volume of the subset of images is dynamically determined based on the requested feature(s) of interest. Additionally, or alternatively, the size of the subset of images may be dynamically determined based on the determined characteristics related to the requested feature(s) of interest.

Global spatio-temporal processing module 120 may be configured to provide a global perspective by processing all subset(s) of images analyzed by local spatio-temporal processing module 110. For example, global spatio-temporal processing module 120 may process the whole input video or set of input images by processing all outputs of local spatio-temporal processing module 110 at once or together. Further, global spatio-temporal processing module 120 may be configured to provide output that includes numerical scores for each image frame by processing the vectors of determined characteristics related to the feature(s) of interests. In some embodiments, global spatio-temporal processing module 120 may process the images and vectors and output refined quality scores and segmentation maps of each image. Further example details related to global spatio-temporal processing module 120 are provided below with reference to the FIG. 3B embodiment.

Timeseries analysis module 130 uses information about images determined by local spatio-temporal processing module 110 and refined by global spatio-temporal processing module 120 to output a numerical score to indicate the presence of the one or more feature(s) of interest requested by a user of intelligent detector system 100. For example, time series analysis module 130 may be configured to use spatial and temporal information of characteristics related to the feature(s) of interest determined by local spatio-temporal processing module 110 to perform timeseries analysis on the input video or images. Further example details related to timeseries analysis module 130 are provided below with reference to the FIG. 3C embodiment.

Task manager 140 may help manage the various tasks requested by users of intelligent detector system 100. A task may relate to a requested or required feature of interest and/or characteristics of a feature of interest. One or more characteristics and features of interest may be part of each task for processing by intelligent detector system 100. Task manager 140 may help manage tasks for detections of multiple features of interest in a set of input images. Task manager 140 may determine the number of instances of components of intelligent detector system 100 (e.g., local spatio-temporal processing module 110, global spatio-temporal processing module 120, and timeseries analysis module 130). Further example details of ways of handling multiple task requests to detect features of interest are provided below with reference to the FIGS. 6 and 7 descriptions below.

Intelligent detector system 100 may receive input video or sets of images from image source 150 via network 160 for processing. In some embodiments, intelligent detector system 100 may receive input video directly from another system, such as a medical instrument or system used to capture video when performing a medical procedure, colonoscopy, for example. After processing the images, reports of detected features of interest may be shared via network 160. As disclosed herein, the reports may be transmitted electronically and take different forms, such as electronic files, displays, and data. In some embodiments, reports are sent as files to and/or displayed at user device 170. Network 160 may take various forms depending on the system needs and environment. For example, network 160 may include or utilize any combination of the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, and/or other types of network communications. In some embodiments, network 160 may include an on-premises (e.g., LAN) network, while in other embodiments, network 160 may include a virtualized, remote, and/or cloud network (e.g., AWS™, Azure™, IBM Cloud™, etc.). Further, network 160 may in some embodiments be a hybrid on-premises and virtualized, remote, and/or cloud network, including components of one or more types of network architectures.

User device 170 may send requests to and receive output (e.g., reports or data) from intelligent detector system 100 related to feature(s) of interest in input video or images. User device 170 may control or directly provide the input video or images to intelligent detector system 100 for processing, including by way instructions, commands, video or image set file download(s), and/or storage link(s) to storage locations (e.g., image source 150). User device 170 may comprise a smartphone, laptop, tablet, computer, and/or other computing device. User device 170 may also include an imaging device (e.g., a video or digital camera) to capture video or images for processing. In the case of capsule examination procedures, for example, user device 170 include a pill cam or similar that is ingested by the user and causes input video or images to be captured and streamed directly to intelligent detector system 100 or stored in image source 150 and subsequently downloaded and received by system 100 via network 160. The results of the image processing are then provided as output from intelligent detector system 100 to user device 170 via network 160.

Physician device 180 may also be used to send requests to and receive output (e.g., reports or data) from intelligent detector system 100 related to feature(s) of interest in input video or images. Similar to user device 170, physician device 180 may control or directly provide the input video or images to intelligent detector system 100 for processing, including by way instructions, commands, video or image set file download(s), and/or storage link(s) to storage locations (e.g., image source 150). Physician device 180 may comprise a smartphone, laptop, tablet, computer, and/or other computing device. Physician device 180 may also include an imaging device (e.g., a video or digital camera) to capture video or images for processing. In the case of video endoscopy examination, for example, physician device 180 may include a colonoscopy probe or similar with an imaging device that captures images during the examination of a patient. The captured video may be streamed as input video to intelligent detector system 100 or stored in image source 150 and subsequently downloaded and received by system 100 via network 160. In some embodiments, physician device 180 may receive a notification for further review of image frames with characteristics of interest. The results of the image processing are then provided as output (e.g., electronic reports or data in the form of files or digital display) from intelligent detector system 100 to user device 170 via network 160.

Image source 150 may include a storage location or other source for input video or images to intelligent detector system 100. Image source 150 may comprise any suitable combination of hardware, software, and firmware. For example, image source 150 may include any combination of a computing device, a server, a database, a memory device, a network communication hardware, and/or other devices. By way of example, image source 150 may include a database, memory, or storage (e.g., storage 220 of FIG. 2) to store input videos or sets of images received from user device 170 and physician device 180. Image source 150 storage may include file storage and/or databases accessed using CPUs (e.g., processors 230 of FIG. 2). As a further example, image source 150 may also include cloud storage, such as AMAZON™ S3, Azure™ Storage, GOOGLE™ Cloud Storage, that is accessible via network 160.

In the example system of FIG. 1A, image source 150, user device 170, and physician device 180 may be local to or remote from one another and may communicate with one another via wired or wireless communications, including via network communications. The devices may also be local to or remote from intelligent detector network 100, depending on the application and needs of the system implementation. Further, while image source 150, user device 170, and physician device 180 are shown in FIG. 1A as being separate from intelligent detector system 100, one or more of these devices may be local to or provided as part system 100. Also, some or part network 160 may be local to or part of system 100. Further, it will be appreciated that the number and arrangement of components and devices in FIG. 1A is provided for purposes of illustration and not intended to limit the invention or disclosed embodiments thereof.

Although embodiments of the present disclosure are described herein with general reference to medical image analysis and endoscopy, it will be appreciated that the embodiments may be applied to other medical image procedures, such as gastroscopy, colonoscopy, and enteroscopy. Further, embodiments of the present disclosure may be implemented for other image capture and analysis environments and systems, such as those for or including LIDAR, surveillance, autopiloting, and other imaging systems.

According to an aspect of the present disclosure, a computer-implemented system is provided for intelligently processing input video or set of images and determining the presence of features of interest and characteristics related thereto. As further disclosed herein, the system (e.g., intelligent detector system 100) may include at least one memory (e.g., a ROM, RAM, local memory, network memory, etc.) configured to store instructions and at least one processor (e.g., processor(s) 230) configured to execute the instruction (see, e.g., FIGS. 1 and 2). Using the at least one processor, the system may process input video or a set of images captured by a medical imaging system, such as those used during an endoscopy, a gastroscopy, a colonoscopy, or an enteroscopy procedure. Additionally, or alternatively, the image frames may comprise medical images, such as images of a gastrointestinal organ or other organ or area of human tissue.

As used herein, the term "image frame" or "image" refers to any digital representation of a scene or field of view captured by an imaging device. The digital representation may be encoded in any appropriate format, such as Joint Photographic Experts Group (JPEG) format, Graphics Interchange Format (GIF), bitmap format, Scalable Vector Graphics (SVG) format, Encapsulated PostScript (EPS) format, or the like. Similarly, the term "video" refers to any digital representation of a scene or area of interest comprised of a plurality of images in sequence. The digital representation of a video may be encoded in any appropriate format, such as a Moving Picture Experts Group (MPEG) format, a flash video format, an Audio Video Interleave (AVI) format, or the like. In some embodiments, the sequence of images for an input video may be paired with audio. As will be appreciated from this disclosure, embodiments of the invention are not limited to processing input video with sequenced or temporally ordered image frames but may also process streamed or stored sets of images captured in sequence or temporally ordered. Accordingly, the terms "input video" and "set(s) of images" should be considered interchangeable and do not limit the scope of the present disclosure.

As disclosed herein, an image frame or image may include representations of a feature of interest (i.e., an abnormality or other object of interest). For example, the feature of interest may comprise an abnormality on or of human tissue. In other embodiments for non-medical procedures, the feature of interest may comprise an object, such as a vehicle, person, or other entity.

In accordance with the present disclosure, an "abnormality" may include a formation on or of human tissue, a change in human tissue from one type of cell to another type of cell, and/or an absence of human tissue from a location where the human tissue is expected. For example, a tumor or other tissue growth may comprise an abnormality because more cells are present than expected. Similarly, a bruise or other change in cell type may comprise an abnormality because blood cells are present in locations outside of expected locations (that is, outside the capillaries). Similarly, a depression in human tissue may comprise an abnormality because cells are not present in an expected location, resulting in the depression.

In some embodiments, an abnormality may comprise a lesion. Lesions may comprise lesions of the gastrointestinal mucosa. Lesions may be histologically classified (e.g., per the Narrow-Band Imaging International Colorectal Endoscopic (NICE) or the Vienna classification), morphologically classified (e.g., per the Paris classification), and/or structurally classified (e.g., as serrated or not serrated). The Paris classification includes polypoid and non-polypoid lesions. Polypoid lesions may comprise protruded, pedunculated and protruded, or sessile lesions. Non-polypoid lesions may comprise superficial elevated, flat, superficial shallow depressed, or excavated lesions. In regards to detecting abnormalities as features of interest, serrated lesions may comprise sessile serrated adenomas (SSA); traditional serrated adenomas (TSA); hyperplastic polyps (HP); fibroblastic polyps (FP); or mixed polyps (MP). According to the NICE classification system, an abnormality is divided into three types, as follows: (Type 1) sessile serrated polyp or hyperplastic polyp; (Type 2) conventional adenoma; and (Type 3) cancer with deep submucosal invasion. According to the Vienna classification, an abnormality is divided into five categories, as follows: (Category 1) negative for neoplasia/dysplasia; (Category 2) indefinite for neoplasia/dysplasia; (Category 3) non-invasive low grade neoplasia (low grade adenoma/dysplasia); (Category 4) mucosal high grade neoplasia, such as high grade adenoma/dysplasia, non-invasive carcinoma (carcinoma in-situ), or suspicion of invasive carcinoma; and (Category 5) invasive neoplasia, intramucosal carcinoma, submucosal carcinoma, or the like. These examples and other types of abnormalities are within the present disclosure. It will also be appreciated that intelligent detector system 100 may be configured to detect other types of features of interest, including for medical and non-medical procedures.

Figure 1B:
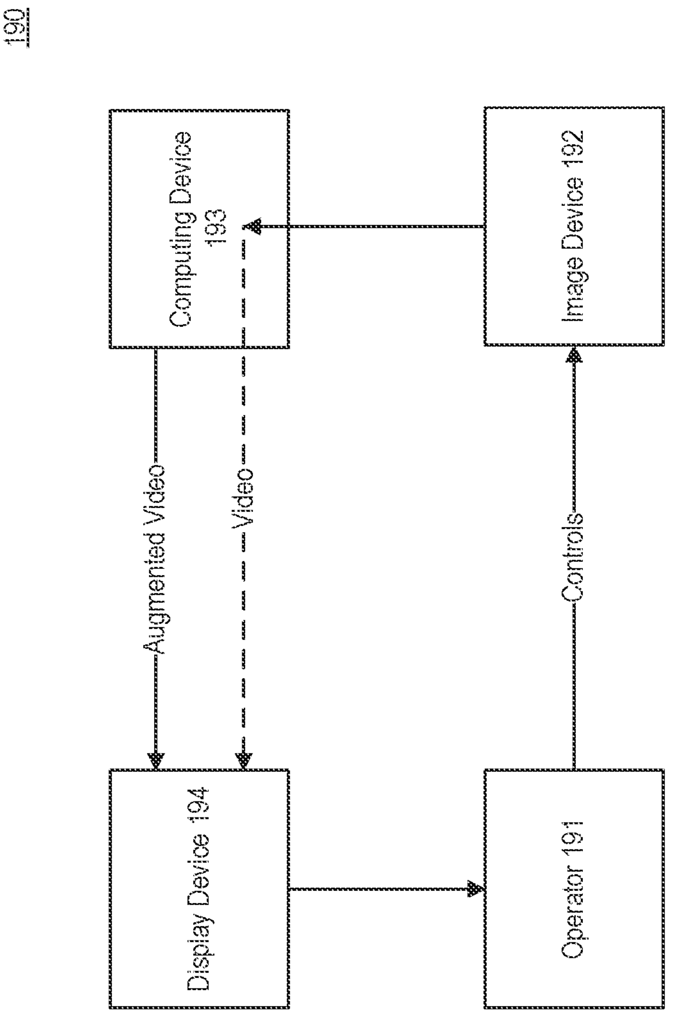
FIG. 1B is a schematic representation of an example computer-implemented system for processing real-time video, consistent with embodiments of the present disclosure.

FIG. 1B is a schematic representation of an example computer-implemented system implementing intelligent detector system 100 of FIG. 1A for processing real-time video, consistent with embodiments of the present disclosure. As shown in FIG. 1B, system 190 includes an image device 192 and an operator 191 who operates and controls image device 192 through control signals sent from operator 191 to image device 192. By way of example, in embodiments where the video feed comprises a medical video, operator 191 may be a physician or other healthcare professional. Image device 192 may comprise a medical imaging device, such as an endoscopy imaging device, or other medical imaging devices that produce videos or one or more images of a human body/tissue/organ or a portion thereof. Image device 193 may be part of physician device 180 (as shown in FIG. 1A), generating videos stored in image source 150. Operator 191 may control image device 192 by controlling, among other things, a capture or frame rate of image device 192 and/or a movement or navigation of image device 192, e.g., through or relative to the human body of a patient or individual. In some embodiments, image device 192 may comprise a swallowable capsule device or another form of capsule endoscopy device as opposed to an endoscopy imaging device inserted through a cavity of the human body.

In the example of FIG. 1B, image device 192 may transmit the captured video as a plurality of image frames directly to a computing device 193. Computing device 193 may comprise memory (including one or more buffers) and one or more processors to process the video or images, as described above and herein (see, e.g., FIG. 2). In some embodiments, one or more of the processors may be implemented as separate component(s) (not shown) that are not part of computing device 193 but in network (e.g., network 160 of FIG. 1A) communication therewith. In some embodiments, the one or more processors of computing device 193 may implement one or more networks, such as trained neural networks. Examples of neural networks include an object detection network, a classification detection network, a location detection network, a size detection network, or a frame quality detection network, as further described herein. Computing device 193 may directly receive and process the plurality of image frames from image device 192. In some embodiments, computing device 193 may use pre and/or parallel processing and buffering to process the video or images in real-time, the level of such processing and buffering being dependent on the frame rate of the received video or images and the processing speed of the one or more processors or modules of computing device 193. As will be appreciated, well-matched processing and buffering capabilities relative to the frame rate will enable real-time processing and output. Further, in some embodiments, control or information signals may be exchanged between computing device 193 and operator 191 for purposes of controlling or instructing the creation of one or more augmented videos as output, the augmented videos including the original video with the addition of an overlay (graphics, symbols, text, and so on) providing information on identified features of interest and other feedback generated by computing device 193 to assist the physician or operator performing the medical procedure. With regard to the exchanged control or information signals, they may be communicated as data through image device 192 or directly from operator 191 to computing device 193. Examples of control and information signals include signals for controlling components of computing device 193, such as an object detection network, a classification detection network, a location detection network, a size detection network, or a frame quality detection network, as described herein.

In the example of FIG. 1B, computing device 193 may process and augment the video received from image device 192 using one or more modules (such as modules 110-140 of intelligent detector system 100) and then transmit the augmented video to a display device 194. Augmented video may provide a real-time feedback and report of, for example, identified polyps and actions taken by operator 191 during or at the end of a medical procedure, such as endoscopy or colonoscopy. Video augmentation or modification may comprise providing one or more overlays, alphanumeric characters, text, descriptions, shapes, diagrams, images, animated images, and/or other suitable graphical representation in or with the video frames. The video augmentation may provide information related to features of interest, such as classification, size, performed actions and/or location information. Additionally or alternatively, the video augmentation may provide information related to one or more recommended action(s) identified by computing device 193 in accordance with a medical guideline. To assist a physician or operator and reduce errors, it will be appreciated that the scope and types of information, reports, and data generated by computing device 193 may be similar to that described above for intelligent detector system 100. Therefore, reference is made to the above examples provided for system 100.

As further depicted in FIG. 1B, computing device 193 may also be configured to relay the original, non-augmented video from image device 192 directly to display device 194. For example, computing device 193 may perform a direct relay under predetermined conditions, such as when there is no overlay or other augmentation to be generated or the image device 192 in turned off. In some embodiments, computing device 193 may perform a direct relay if operator 191 transmits a command as part of a control signal to computing device 193 to do so. The commands from operator 191 may be generated by operation of button(s) and/or key(s) included on an operator device and/or an input device (not shown), such as a mouse click, a cursor hover, a mouseover, a button press, a keyboard input, a voice command, an interaction performed in virtual or augmented reality, or any other input.

To augment the video, computing device 193 may process the video from image device 192 and create a modified video stream to send to display device 194. The modified video may comprise the original image frames with the augmenting information to be displayed to the operator via display device 194. Display device 194 may comprise any suitable display or similar hardware for displaying the video or modified video, such as an LCD, LED, or OLED display, an augmented reality display, or a virtual reality display.

Figure 2:
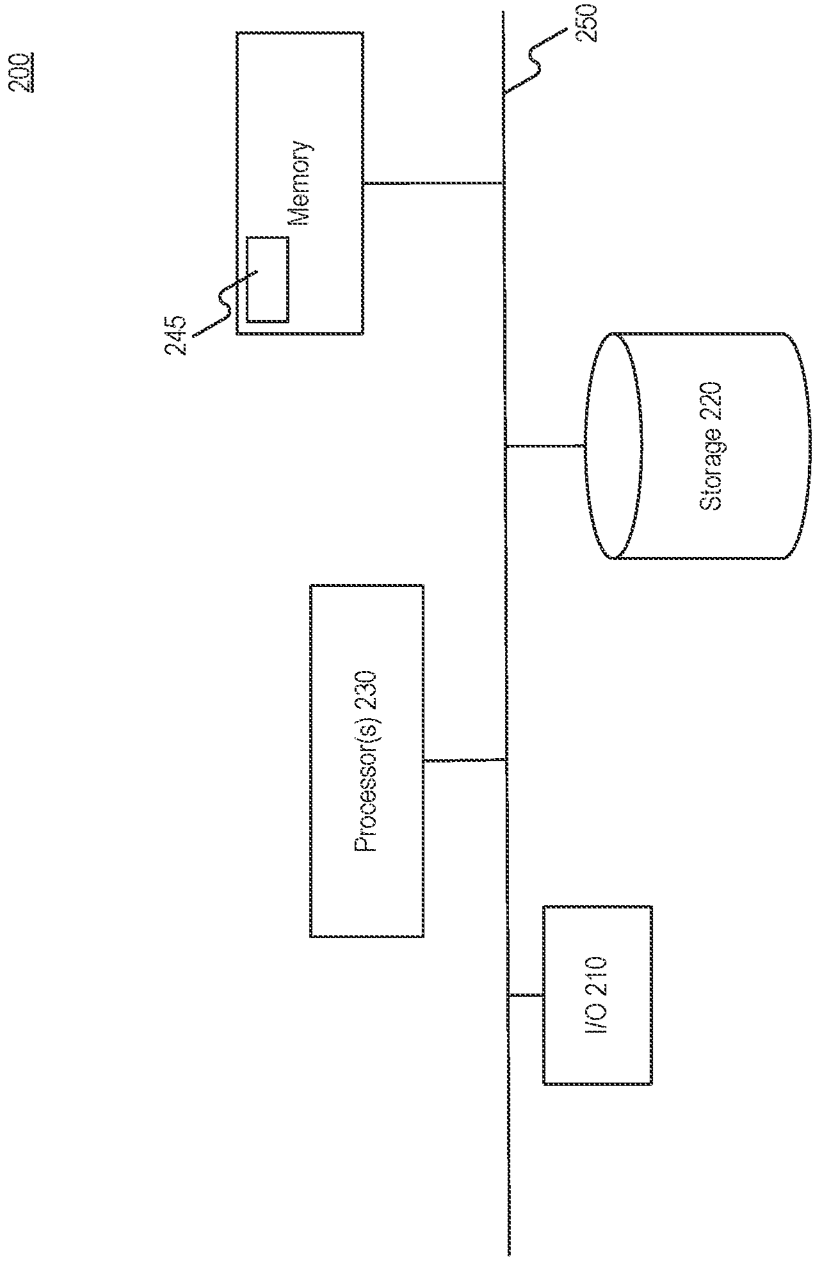
FIG. 2 illustrates an example computing device which may be employed in connection with implementing the example system of FIG. 1A or 1B or other embodiments of the present disclosure.

FIG. 2 illustrates an example computing device 200 which may be employed in connection with implementing the example system of FIG. 1A and other embodiments of the present disclosure. Computing device 200 may be used in connection with the implementation of one or more components of the example system of FIG. 1A (including, e.g., system 100 and devices 150, 170, and 180). In some embodiments, computing device 200 may include multiple sub-systems, such as cloud computing systems, servers, and/or any other suitable components for receiving and processing input video and images.

As shown in FIG. 2, computing device 200 may include one or more processor(s) 230, which may include, for example, one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations, as noted above. In some embodiments, processor(s) 230 may include, or may be a component of, a larger processing unit implemented with one or more processors. The one or more processors 230 may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of data or information.

As further shown in FIG. 2, processor(s) 230 may be communicatively connected via a bus or network 250 to a memory 240. Bus or network 250 may be adapted to communicate data and other forms of information. Memory 240 may include a memory portion 245 that contains instructions that when executed by the processor(s) 230, perform the operations and methods described in detail herein. Memory 240 may also be used as a working memory for processor(s) 230, a temporary storage, and other memory or storage roles, as the case may be. By way example, memory 240 may be a volatile memory such as, but not limited to, random access memory (RAM), or non-volatile memory (NVM), such as, but not limited to, flash memory.

Processor(s) 230 may also be communicatively connected via bus or network 250 to one or more I/O device 210. I/O device 210 may include any type of input and/or output device or periphery device, including keyboards, mouses, display devices, and so on. I/O device 210 may include one or more network interface cards, APIs, data ports, and/or other components for supporting connectivity with processor(s) 230 via network 250.

As further shown in FIG. 2, processor(s) 230 and the other components (210, 240) of computing device 200 may be communicatively connected to a database or storage 220. Storage 220 may electronically store data (e.g., input video or sets of images, as well as reports and other output data) in an organized format, structure, or set of files. Storage 220 may include a database management system to facilitate data storage and retrieval. While illustrated in FIG. 2 as a single device, it is to be understood that storage 220 may include multiple databases or storage devices either collocated or distributed. In some embodiments, storage 220 may be implemented in whole or part as part of a remote network, such as a cloud storage.

Processor(s) 230 and/or memory 240 may also include machine-readable media for storing software or sets of instructions. "Software" as used herein refers broadly to any type of instructions, whether referred to as software, firmware, middleware, microcode, hardware description language, or otherwise. Instructions may include code (e.g., in source code format, binary code format, executable code format, or any other suitable format of code). The instructions, when executed by one or more processors 230, may cause the processor(s) to perform the various operations and functions described in further detail herein.

Implementations of computing device 200 are not limited to the example embodiment shown in FIG. 2. The number and arrangement of components (210, 220, 230, 240) may be modified and rearranged. Further, while not shown in FIG. 2, computing device 200 may be in electronic communication with other network(s), including the Internet, a local area network, a wide area network, a metro area network, and other networks capable of enabling communication between the elements of the computing architecture. Also, computing device 200 may retrieve data or other information described herein from any source, including storage 220 as well as from network(s) or other database(s). Further, computing device 200 may include one or more machine-learning models used to implement the neural networks and other modules described herein and may retrieve or receive weights or parameters of machine-learning models, training information or training feedback, and/or any other data and information described herein.

Figure 3A:
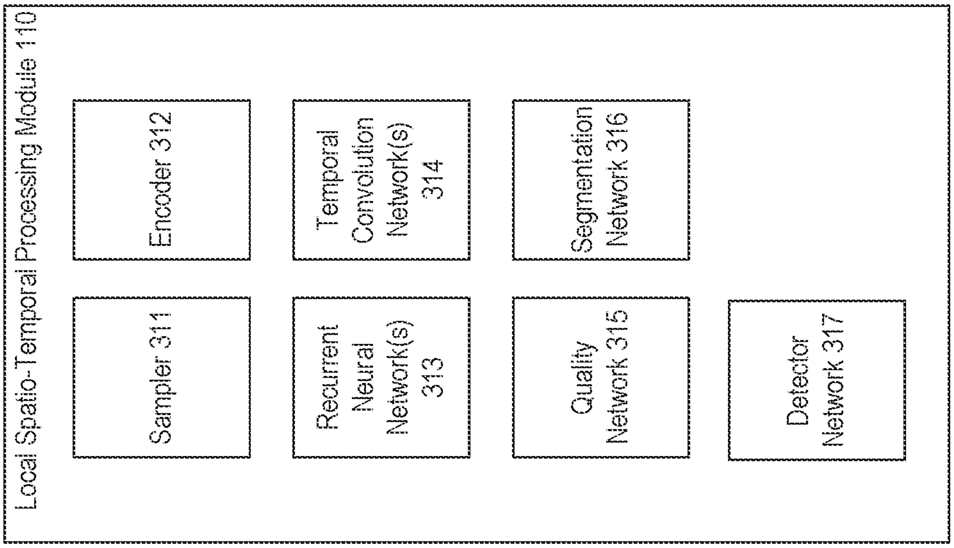
FIG. 3A is a block diagram of an example local spatio-temporal processing module, consistent with embodiments of the present disclosure.

FIG. 3A is a block diagram of an example local spatio-temporal processing module, consistent with embodiments of the present disclosure. The embodiment of FIG. 3A may be used to implement local spatio-temporal processing module 110 of the example intelligent detector system 100 of FIG. 1A or other computer-implemented systems such as computing device 193 in FIG. 1B. As illustrated in FIG. 3A, local spatio-temporal processing module 110 includes a number of components, including a sampler 311, an encoder 312, a recurrent neural network (RNN) 313, a temporal convolution network (TCN) 314, a quality network 315, and a segmentation network 316. These components may be implemented with any suitable combination of hardware, software and firmware, and used to select and process subsets of images. Local spatio-temporal processing module 110 may apply various networks iteratively to the whole input video or set of images (with T image frames) using as input batches of N image frames (where N>=1). Such image frames could be consecutive or sampled at a fixed rate from the input video or set of images.

Sampler 311 may select the image frames for processing by other components of local spatio-temporal processing module 110. In some embodiments, sampler 311 may buffer an input video or set of images for a set period and extract image frames in the buffer as subsets of images for processing by module 110. In some embodiments, sampler 311 may allow the configuration of the number of frames or size of the image subsets to select for processing by local spatio-temporal processing module 110. For example, sampler 311 may be configured to receive user input that sets or tunes the number of frames or size of image subsets for processing. Additionally, or alternatively, sample 311 may be configured to automatically select the number of image frames or size of image subsets based on other factors, such as the requested feature(s) of interest for processing and/or the characteristics related to the feature(s) of interest. In some embodiments, the amount or size of sampled images may be based on the frame rate of the video (24, 30, 60, and 120 FPS). For example, sampler 311 may periodically buffer a real-time video stream received by intelligent detector system 100 for a set period to extract images from the buffered video. As a further example, a stream of images from a pill cam or other imaging device may be buffered and the images for processing by system 100 may be extracted from the buffer. In some embodiments, sampler 311 may selectively sample images based on other factors such as video quality, length of the video, characteristics related to the requested feature(s) of interest, and/or the feature(s) of interest. In some embodiments, sampler 311 may sample image frames based on components of local spatio-temporal processing module 110 involved in performing a task requested by a user of intelligent detector system 100. For example, encoder 312 using a 3D encoder network may require multiple images to create a three-dimensional structure of the content to encode.

Encoder 312 may determine the presence of characteristics related to each feature of interest that is part of a task requested by a user of intelligent detector system 100. For image analysis, encoder 312 may be implemented using a trained convolution neural network. Intelligent detector system 100 may include a 2D encoder and a 3D encoder containing non-local layers as encoder 312. Encoder 312 may be composed of multiple convolutional residual and fully connected layers. Depending on the characteristics and features of interest to be detected, encoder 312 may select a 2D or 3D convolutional encoder. Encoder 312 may be trained to detect characteristics in an image that are required to detect requested feature(s) of interest in the image frames. As disclosed herein, Intelligent detector system 100 may process images and detect desirable characteristics related to the feature(s) of interest using encoder 312. Intelligent detector system 100 may determine the desirable characteristics based on the trained network of encoder 312 and past determinations of feature(s) of interest.

As shown in FIG. 3A, local spatio-temporal processing module 110 may also be equipped with recurrent neural networks (RNNs) 313. RNNs 313 may work with encoder 312 to determine the presence of desirable characteristics related to feature(s) of interest. In some embodiments, temporal convolution networks (TCNs) 314 may also be used to assist with detecting such characteristics in each image frame of an input video. TCNs are specialized convolution neural networks that can handle sequences of images such as the temporally ordered set of images that are frames of an input video from a source (e.g., image source 150 of FIG. 1A or image device 192 in FIG. 1B). TCNs can work on a subset of images of all image frames of an input video buffered to be processed by local processing module 110 or all images of input video processed by global processing module 120. TCNs can process sequential data using causal convolutions in a fully connected convolution network.

RNNs 313 are artificial neural networks with internal feedback connections and an internal memory status used to determine spatio-temporal information in the image frames. In some embodiments, RNNs 313 may include local layers to improve its capability of aggregating spatio-temporal information spatially and/or temporally apart in buffered image frames selected by sampler 311. RNNs 313 can be configured to associate a score, e.g., between 0 and 1, for each desirable characteristic related to a requested feature of interest. The score indicates the likelihood of the presence of the desirable characteristic in an image, with 0 being least likely and 1 being a maximum likelihood.

As shown in FIG. 3A, local spatio-temporal processing module 110 may include additional components, such as a quality network 315 and a segmentation network 316, to further assist with the identification of characteristics required to detect features of interest in processed images. For example, quality network 315 may be implemented as a neural network composed of several convolutional layers and several fully connected layers that improve final scores assigned to image frames. For example, quality network 315 may filter out image frames with a low characteristic scores. Quality network 315 may also generate feature vectors based on the determined characteristics for each image frame. Each feature vector may provide a quality score represented as an ordinal number [0, R] indicating the frame image quality, with 0 being the minimum quality, R being the maximum quality. Quality network 315 may automatically set a quality score of 0 for those characteristics not detected in an image.

Segmentation network 316 may process the images to compute for each input image a segmentation mask to extract a segment of the image, including characteristics related to a feature of interest. A segmentation mask may be a pixel-wise binary mask with a resolution that is the same as or less than that of the input image. Segmentation network 316 may be implemented as a deep convolutional neural network including multiple convolutional residual layers and multiple skip-connections. The number of layers and type of layers included in a segmentation network may be based on the characteristics or requested feature of interest. In some embodiments, a single model with multiple layers may handle tasks of encoder 312 and segmentation network 316. For example, a single model can be a U-Net model with a ResNet encoder.

By way of example, segmentation network 316 may take an image with dimensions W×H as input and return a segmentation mask represented by a matrix with dimensions W'×H', where W' is lesser than or equal to W and H' is lesser than or equal to H. Each value in the output matrix represents the probability that certain image frame coordinates contain characteristics associated with the requested feature of interest. In some embodiments, intelligent detector system 100 may produce multiple output matrices for multiple features of interest. The multiple matrices may vary in dimensions.

Figure 3B:
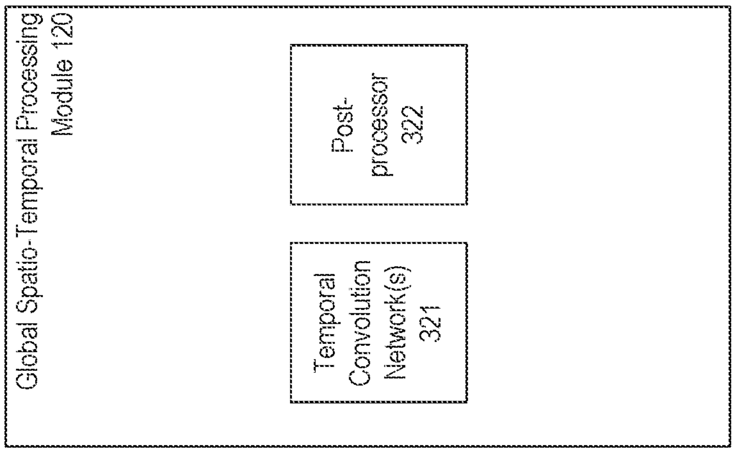
FIG. 3B is a block diagram of an example global spatio-temporal processing module, consistent with embodiments of the present disclosure.

FIG. 3B is a block diagram of an example global spatio-temporal processing module, consistent with embodiments of the present disclosure. The embodiment of FIG. 3B may be used to implement global spatio-temporal processing module 120 of the example intelligent detector system 100 of FIG. 1A or other computer-implemented systems such as computing device 193 in FIG. 1B. Global spatio-temporal processing module 120 may modify or refine the outputs obtained from local spatio-temporal processing module 110. Thus, global spatio-temporal processing module 120 may be configured to process the complete set of images together subsequent to local spatio-temporal processing module 110 processing all subsets of images of input video obtained from, e.g., image source 150 over network 160. By way of example, global spatio-temporal processing module 120 processes the output of the complete set of images processed by local spatio-temporal processing module 110 to modify the output thereof by refining and filtering outliers in images with determined characteristics or features of interest. In some embodiments, global spatio-temporal processing module 120 may refine quality scores and segmentation masks generated by quality network 315 and segmentation network 316.

Global spatio-temporal processing module 120 may refine the scores of determined characteristics using one or more non-causal temporal convolutional networks (TCN) 321. Global spatio-temporal processing module 120 can process the output of all images processed by local spatio-temporal processing module 110 using dilated convolutional networks included as TCNs 321. Such dilated convolution networks help to increase receptive field without increasing the network depth (number of layers) or the kernel size and can be used for multiple images together.

As further disclosed herein, TCNs 321 may review a whole timeseries of features K×T' extracted using local spatio-temporal processing module 110. TCNs 321 may take as input matrix of features of K×T' dimensions and return one or more multiple timeseries of scalar values of length T".

Global spatio-temporal processing module 120 may refine quality scores generated by quality network 315 using one or more signal processing techniques such as low-pass filters and Gaussian smoothing. In some embodiments, global spatio-temporal processing module 120 may refine segmentation masks generated by segmentation network 316 using a cascade of morphological operations. Global spatio-temporal processing module 120 may refine binary mask for segmentation by using prior information about shape and distribution of the determined characteristics across input images identified by encoder 312 in combination with RNNs 313 and causal TCNs 314.

TCNs 321 may work on the complete video or sets of input images and thus need to wait on local spatio-temporal processing module 110 to complete processing individual image frames. To accommodate this requirement, TCNs 321 may be trained following the training of the networks in local spatio-temporal processing module 110. The number and architecture of layers of TCNs 321 is dependent on the task(s) requested by a user of intelligent detector system 100 to detect certain feature(s) of interest. TCNs 321 may be trained based on requested feature(s) of interest to be tasked to the system. A training algorithm for TCNs 321 may tune parameters of TCNs 321 for each such task or feature of interest.

By way of example, intelligent detector system 100 may train TCNs 321 by first computing K-dimensional timeseries for each video in training set 415 using local spatio-temporal processing module 110 and applying a gradient-descent based optimization to estimate TCNs 321 parameters to minimize loss function L (s, s'), where s is the estimated output timeseries of scores, and s' is the ground truth timeseries. Intelligent detector system 100 may calculate the distance between s and s' using, e.g., mean squared error (MSE), cross entropy, and/or Huber loss.

Similar to training processes for other neural networks, data augmentation, learning rate tuning, label smoothing, and/or batch training may be used when training TCNs 321 to improve its capabilities and the results.

Intelligent detector system 100 may be adapted to a specific requirement by tuning hyperparameters of components 110-130. In some embodiments, intelligent detector system 100 may modify the pipeline's standard architecture to process input video or sets of images by adding or removing components 110-130 or certain parts of components 110-130. For example, if intelligent detector system 100 needs to address a very local task, it may drop the usage of TCNs 321 in global spatio-temporal processing module 120 to avoid any global spatio-temporal processing of output generated by local spatio-temporal processing module 110. As another example, if a user of intelligent detector system 100 requests a diffuse task, RNNs 313 and/or TCNs 314 may be removed from local spatio-temporal processing module 110. Intelligent detector system 100 may remove global spatio-temporal processing module 120 or some RNNs 313 and TCNs 314 of local spatio-temporal processing module 110 by deactivating the relevant networks from the pipeline used for processing input video or images to detect requested pathologies.

Other arrangements or implementations of the system are also possible. For example, segmentation network 316 may be unnecessary and dropped from the pipeline when the requested task for detecting features of interest does not deal with focal objects in image frames of the images. As another example, quality network 315 may be unnecessary and deactivated when all image frames are regarded useful. For example, when the frame rate of input video is low or has too many image frames with errors, then intelligent detector system 100 may avoid further filtering image frames by using quality network 315. As will be appreciated from this disclosure, intelligent detector system 100 may pre-process and/or sample input video or images to determine the components that need to be active and trained as part of local spatio-temporal processing module 110 and global spatio-temporal processing module 120.

Figure 3C:
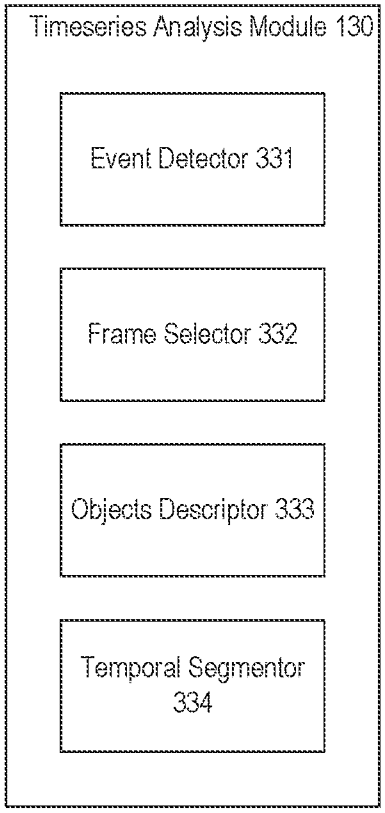
FIG. 3C is a block diagram of an example timeseries analysis module, consistent with embodiments of the present disclosure.

FIG. 3C is a block diagram of an example timeseries analysis module, consistent with embodiments of the present disclosure. The embodiment of FIG. 3C may be used to implement timeseries analysis module 130 of the example intelligent detector system 100 of FIG. 1A or other computer-implemented systems such as computing device 193 in FIG. 1B. Timeseries analysis module 130 may use scores, quality values, and segmentation maps for each image frame processed by local spatio-temporal processing module 110 as input to generate the final output score for each image. In some embodiments, after a completion of a medical procedure, timeseries analysis module 130 may use scores, quality values, and/or segmentation maps of images produced by local spatio-temporal processing module to generate a dashboard or other display with a summary of quality scores of all images. Components of time series analysis module 130 may be used to generate different output scores and values that are presented as an aggregated summary for the images processed by intelligent detector system 100. As illustrated in FIG. 3C, timeseries analysis module 130 components may include an event detector 331, a frame selector 332, an objects descriptor 333, and a temporal segmentor 334 to help generate the final output scores for images of an input video.

Event detector 331 may determine the start and stop times in an input video of an event associated with a requested feature of interest. In some embodiments, event detector 331 determines the start and end image frame in an input video of events associated with a requested feature of interest. In some embodiments, the start and stop times or image frames of events may overlap.

The start and stop times of the events may be the beginning and end of portions of the input video where some of the characteristics related to a feature of interest are detected. The start and stop times of video may be estimations due to missing image frames from the analysis by local spatio-temporal processing module 110. Event detector 331 may output a list of pairs (t, d), where t is a time instance and d is the description of the event detected at that time. Various events may be identified based on different features of interest processed by intelligent detector system 100.

Portions of the input video identified from events may include portions of an organ scanned by a healthcare professional or other operator to generate input video as part of a medical procedure. For example, a medical procedure such as a colonoscopy may include events configured for various portions of a colon, such as ascending colon, transverse colon, or descending colon.

Timeseries analysis module 130 may provide a summary report of the events of different portions of the video that represent different portions of a medical procedure. The summary report may include, for example, the length of video or time taken to complete a scan of a portion of the organ associated with the event, which may be listed as a withdrawal time. Event detector 331 may help generate the summary report of different portions of medical procedure that include events related to the features of interest.

Timeseries analysis module 130 may present summary report(s) of different portions of a medical procedure video (e.g., colonoscopy video) on a dashboard or other display showing, e.g., pie charts with the amount of video requiring different actions on the portion of the video or portion of the organ represented by the video portion, such as careful second review, performing a biopsy, or removing a lesion. In some embodiments, the dashboard may include quality summary details of events identified by event detector 331 in a color-coded manner. For example, the dashboard may include red, orange, and green colored buttons or other icons to identify the quality of video of a portion of a medical procedure representing an event. The dashboard may also include summary details of the overall video representing the whole medical procedure with same level of information as that provided for individual portions of the medical procedure.

In some embodiments, the summary report generated by timeseries analysis module 130 may identify one or more frames to review portion(s) more carefully and/or address other issues. The summary report may also indicate what percentage of the video to conduct additional operations, such as second review. Timeseries analysis module 130 may use frame selector 332 to identify specific frames of the video or the percentage of video to conduct additional operations.

Frame selector 332 may retrieve image frames in the input video based on the characteristics and scores generated by local spatio-temporal processing module 110. In some embodiments, frame selector 332 may also utilize the user provided quality values to select image frames. Frame selector 332 may select image frames based on their relevance to characteristics and/or features of interest requested by a user of intelligent detector system 100.

In some embodiments, the summary report generated by timeseries analysis module 130 may include one or more image frames identified by frame selector 332. An image frame presented in the report may be augmented to display marking(s) applied to one or more portions of the frame. In some embodiments, markings may identify a feature of interest such as a lesion or polyp in an image frame. For example, a colored bounding box may be used as a marking surrounding the feature of interest (see, e.g., FIG. 10 and the green bounding boxes applied to the image frames shown therein). In some embodiments, different markings (including different combinations of shape(s) and/or color(s)) may be used to indicate different features of interest. For example, an image frame may be augmented to include one or more markings in the form of bounding boxes of different colors representing different features of interest identified by intelligent detector system 100.

Objects descriptor 333 may merge image frames of input video that include matching characteristics from the requested features of interest. Objects descriptor merges image frames based on temporal and spatial coherence information provided local spatio-temporal processing module 110. Objects descriptor 333 output may include a set of objects described using sets of properties. Property sets may include a timestamp of image frames relative to other image frames of the input video. In some embodiments, property sets may include statistics on estimated scores and locations of detected characteristics or requested features of interest in image frames.

Temporal segmentor 334 splits an input video into temporal intervals. Temporal segmentor 334 may split based on coherence on task to determine requested features of interest. Temporal segmentor 334 may output a label for each image frame of the input video in the form {L_i}. The output labels may indicate the presence and probability of a requested feature of interest in an image frame and position within the image frame. In some embodiments, temporal segmentor 334 may output separate labels for each feature of interest in each image frame.

In some embodiments, timeseries analysis module 130 may generate a dashboard or other display including quality scores for a medical procedure performed by a physician, healthcare professional, or other operator. To provide the quality scores, time analysis module 130 may include machine learning models that are trained based on videos of the medical procedure performed by other physicians and operators with different examination performance behaviors. Among other things, machine learning models may be trained to recognize video segments during which the examination behavior of the healthcare professional indicates the need for additional review. For example, an endoscopist carefully exploring the colon/small bowel surface, as opposed to the time he spends cleaning it or performing surgeries or navigating etc. may indicate requirement of additional review of the small bowel surface. Machine learning models used by timeseries analysis module 130 may learn about particular activity of a healthcare professional such as careful exploration based on the amount of time spent, number of pictures taken, and/or number of repeated scans of a certain section of a medical procedure representing certain portion of an organ. In some embodiments, machine learning model may learn about healthcare professional behavior based on the amount of markings in the form of notes or flags added to the video or certain areas of the image frame in a video.

In some embodiments, timeseries analysis module 130 may generate a summary report of quality scores of a healthcare professional behavior using information about the time spent performing certain actions (e.g., careful exploration, navigating, cleaning, etc.). In some embodiments, the percentage of total time of medical procedure for a certain action may be used for calculating the quality score of the medical procedure or a portion of the medical procedure. Timeseries analysis module 130 may be configured to generate a quality summary report of healthcare professional behavior based on the configuration of intelligent detector system 100 to include actions performed by the healthcare professional as features of interest.

To generate a dashboard with the summary scores described above, timeseries module may utilize event detector 331, frame selector 332, object descriptor 333, and temporal segmentor 334 in combination. The dashboard may include one or more frame(s) from the medical procedure that are selected by frame selector 332 and information regarding the total time spent on the medical procedure and the time spent examining portions with pathologies or other features of interest. The quality score summary of statistics describing healthcare professional behavior may be computed for the whole medical procedure (e.g., whole colon scan) and/or for portion(s) identifying an anatomical region (e.g., colon segments such as ascending colon, transverse colon, and descending colon).

Timeseries analysis module 130 may use event detector 331, frame selector 332, object descriptor 333, and temporal segmentor 334 to generate aggregate information about different features of interest, such as different regions of an organ captured during a medical procedure, the presence of each pathology, and/or actions of a healthcare professional performing the medical procedure. For example, aggregate information may be generated based on a listing of the various pathologies in different regions using object descriptor 333, frame(s) showing a pathology selected by frame selector 332, and an identified amount of time spent in the region of each pathology and the healthcare professional actions determined by event detector 331.

In some embodiments, timeseries analysis module 130 may generate a summary of input video processed by local spatio-temporal processing module 110 and global spatio-temporal processing module 120. Summary of input video may include segments of input video extracted and combined into a summary of the input video with features of interest. In some embodiments, the user can choose whether to view only the summary video or to expand each of the interval of the video which were discarded by the module. Temporal segmentor 334 of timeseries analysis module 130 may help extract portions of input video with features of interest. In some embodiments, timeseries analysis module 130 may generate a video summary by selecting relevant frames to generate a variable frame rate video output. Frame selector 332 of timeseries analysis module 130 may aid in the selection and dropping of frames in an output video summary. In some embodiments, timeseries analysis module 130 may provide additional metadata to the input video or a video summary. For example, timeseries analysis module 130 may color code the timeline of an input video where features of interest are present in an input video. Timeseries analysis module 130 may use different colors to highlight a timeline with different features of interest. In some embodiments, the portions of output video summary with features of interest may include overlayed text and graphics on the output video summary.

In some embodiments, to maximize performance modules 110-130 may be trained to select optimal parameter values for the neural networks in each of the modules 110-130.

The components of local spatio-temporal processing module 110 shown in FIG. 3A may include neural networks that are trained in advance of being used to process images and detect characteristics related to features of interest. Neural networks in local spatio-temporal processing module 110 may be trained based on a video dataset including three subsets: training set 415, validation set 416, and test set 417 (see FIG. 4A). The training subsets for intelligent detector system 100 may require labeled video sets. For example, a labeled video set may include a target score assigned to the video processing by components of intelligent detector system 100. A labeled video set may also include the location of characteristics detectable in each image frame of the video set and the value of each characteristic. Both labels and input video sets may be used for training purposes. In some embodiments, labels for a subset of a video set may be used to determine labels of other subsets used for training neural networks in components 110-130 of intelligent detector system 100.

During the training process, intelligent detector system 100 may sample from training dataset images or a buffer of images processed by the neural networks in components 110-130 of intelligent detector system 100 and updates their parameters by error backpropagation. Intelligent detector system 110 may control the convergence of ground truth value y' of a desirable characteristic and encoder 312 output value y using validation set 416 of a video set. Intelligent detector system 100 may use test set 417 of a video set to assess the performance of encoder 312 to determine values of characteristics in image frames of a training subset of a video set. Intelligent detector system 100 may continue to train until the ground truth value y' converges with the output value y. Intelligent detector system 100 upon reaching convergence may complete the training procedure and remove the temporary fully connected network. Intelligent detector system 100 finalizes encoder 312 for the latest value of parameters.

Figure 4A:
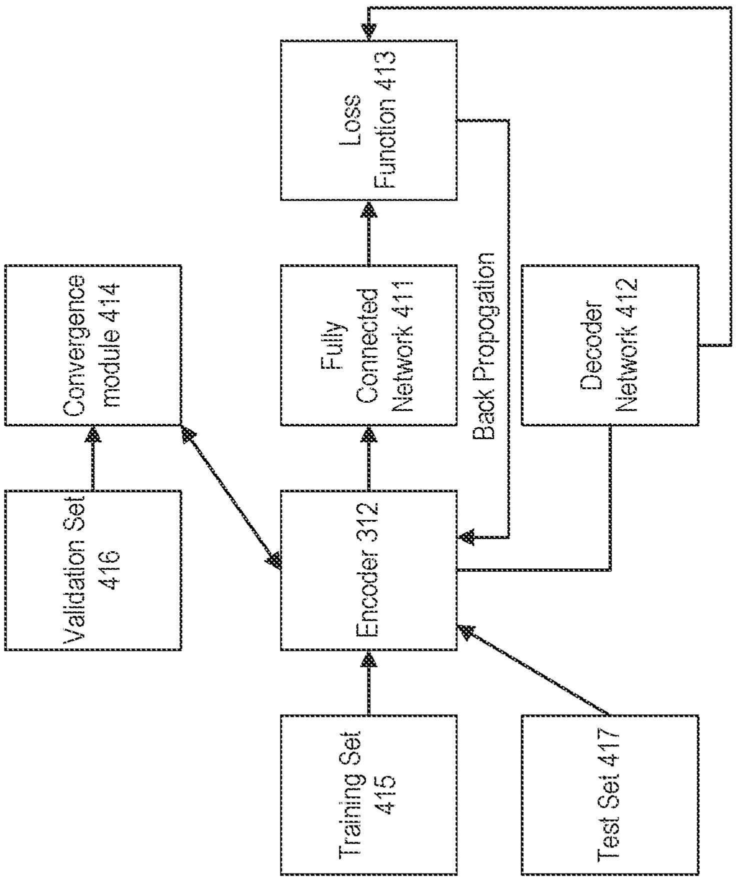
FIG. 4A is a flow diagram illustrating example training of an encoder component of the local spatio-temporal processing module of FIG. 3A, consistent with embodiments of the present disclosure.

FIG. 4A is a flow diagram illustrating example training of an encoder component of the local spatio-temporal processing module of FIG. 3A, consistent with embodiments of the present disclosure. An encoder component such as encoder 312 for FIG. 3A takes a single image frame or a small buffer of N image frames as input and produces a feature vector of M dimension as output. As illustrated in FIG. 4A, Intelligent detector system 100 may train encoder 312 by adding a temporary network. Temporary network may be fully connected network (FCN) 411 added as an additional layer at the end of encoder 312 to train encoder 312. FCN 411 may take as input feature vector of each image frame of input generated by encoder 312 and returns a single float value or a one-hot vector y. Intelligent detector system 100 may use loss function 413 to evaluate the convergence of ground truth value y' and encoder 312 output y. Loss function may be an additional layer added as the last layer of encoder 312. Loss function 413 may be represented as L(y,y'), indicating the distance between ground truth value for a characteristic y' to output y generated by encoder 312 for an image frame of an input video. Intelligent detector system 100 may use mean squared error (MSE), cross entropy, or Huber loss as loss function 413 for training encoder 312 using FCN 411.

In some embodiments, the temporary network may be decoder network 412 used by intelligent detector system 100 to train encoder 312. Decoder network 412 may be a convolutional neural network that maps each feature vector estimated by encoder 312 to a large matrix (I_out) of the same dimensions as an image frame (I_in) of an input video. Decoder network 412 may use L(I_out, I_in) as loss function 413 to compute the distance between two images (or buffers of N images). Loss function 413 used with decoder network 412 may include mean squared error (MSE), structural similarity (SSIM), or L1 norm. Decoder network 412 used as a temporary network to train encoder 312 does not require the determination of ground truth values for the training/validation/testing subsets 415-417 of a video set. Intelligent detector system 100 training encoder 312 using decoder network 412 as the temporary network may control convergence with validation set 416 and use test set 417 to assess the expected performance of encoder 312. Intelligent detector system 110 may drop or deactivate decoder network 412 after completing encoder 312 training.

In both training methods using fully connected network 411 and decoder network 412, encoder 312 and other components of intelligent detector system 100 may use techniques such as data augmentation, learning rate tuning, label smoothing, mosaic, MixUp, and CutMix data augmentation, and/or batch training to improve the training process of encoder 312. In some embodiments, neural networks in intelligent detector system 100 may suffer from class imbalance and may use ad-hoc weighted loss functions and importance sampling to avoid a prediction bias for the majority class.

Figure 4B:
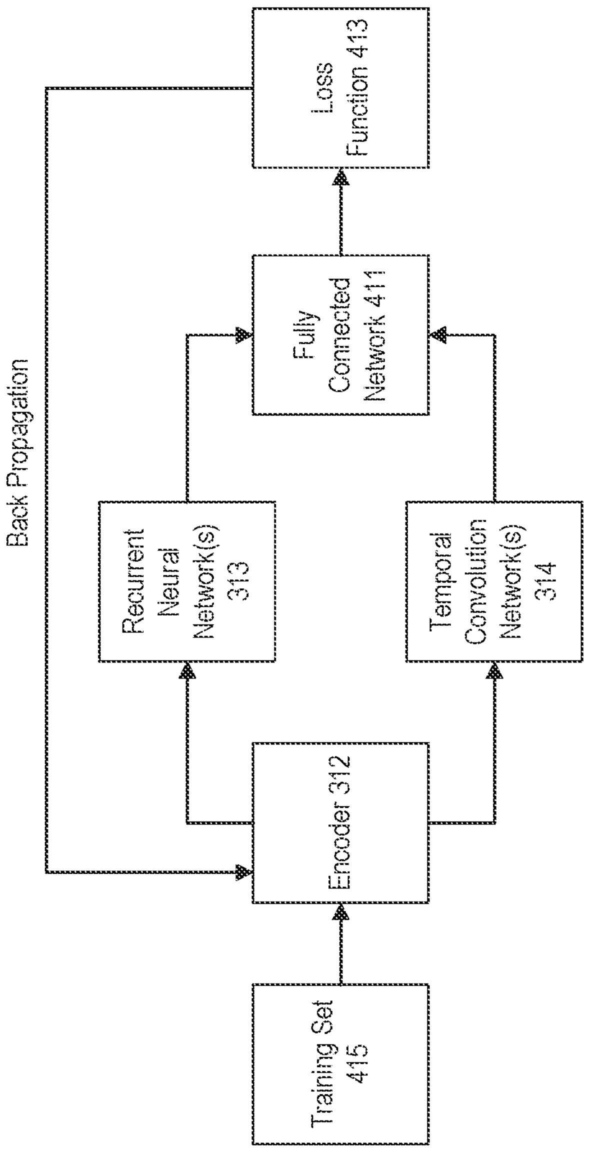
FIG. 4B is a flow diagram illustrating example training of neural network component(s) of the local spatio-temporal processing module of FIG. 3A, consistent with embodiments of the present disclosure.

FIG. 4B is a flow diagram illustrating example training of neural network component(s) of the example local spatio-temporal processing module of FIG. 3A. The example training of FIG. 4B may be used for training, for example, recurrent neural networks (RNNs) 313 and temporal convolution networks (TCNs) 314 of local spatio-temporal processing module 110, consistent with embodiments of the present disclosure. Training Deep Neural Networks (DNN) in intelligent detector system 100 such as RNNs 313 and TCNs 314 may require preparing a set of annotated videos or images and a loss function during the training procedure. During the training procedure, intelligent detector system 100 may adjust the network parameters using gradient-descent based optimization algorithms.

Intelligent detector system 100 may train RNNs 313 and TCNs 314 using the output of a previously trained encoder 312. The input to RNNs 313 and TCNs 314 may be an M-dimensional feature vector per time instant output by encoder 312. RNNs 313 and TCNs 314 aggregate multiple feature vectors generated by encoder 312 by buffering feature vectors generated by encoder 312. Intelligent detector system 100 may train RNNs 313 and TCNs 314 by feeding a sequence of consecutive image frames encoder 312 and passing the generated feature vectors to RNNs 313 and TCNs 314. For a sequence of B images (or buffered sets of images), encoder 312 produces B vectors of M encoded features and sent to RNNs 313 or TCNs 314 to produce B vectors of K features.

Intelligent detector system 100 may train RNNs 313 and TCNs 314 by including a temporary fully connected network (FCN) 411 at the end of RNNs 313 and TCNs 314. FCN 411 converts K dimensional feature vector generated by RNNs 313 or TCNs 314 to a one-dimensional score and compares against ground truth in loss function to revise parameters until there is a convergence between output vector and ground truth vector. In some embodiments, intelligent detector system 100 improves RNNs 313 and TCNs 314 by using data augmentation, learning rate tuning, label smoothing, batch training, weighted sampling, and/or importance sampling as part of training RNNs 313 and TCNs 314.

Figure 4C:
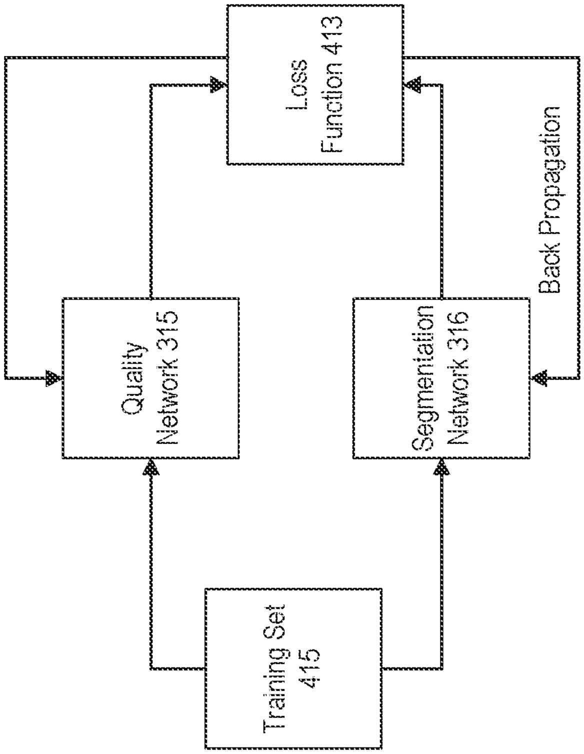
FIG. 4C is a flow diagram illustrating example training of quality network and segmentation network components of the local spatio-temporal processing module of FIG. 3A, consistent with embodiments of the present disclosure.

FIG. 4C is a flow diagram illustrating example training of quality network and segmentation network components of the local spatio-temporal processing module of FIG. 3A. The example training of FIG. 4C may be used for training quality network 315 and segmentation network 316 of the example local spatio-temporal processing module 110, consistent with embodiments of the present disclosure. Intelligent detector system 100 may train quality network 315 similar to the training of encoder 312 but does not need a temporary network (FCN 411 or Decoder network 412 of FIG. 4A). Quality network 315 outputs a scalar value q representing the quality of an image. Intelligent detector system 100 may train quality network 315 by comparing its output quality score q to ground truth quality score q' associated with each image frame of training set 415 of a video set until the difference between the values is minimal. Intelligent detector system 100 may use loss function 413 represented as L(q,q') to minimize the difference between the ground truth value q' and the output quality score q and adjust parameters of quality network 315. Intelligent detector system 100 may train quality network 315 with an MSE, L1 norm as loss function 413. Intelligent detector system 100 may use data augmentation, learning rate tuning, label smoothing, and/or batch training techniques to improve training results of quality network 315.

Intelligent detector system 100 may train segmentation network 316 using one or more individual images or small buffer with size N. The buffer size N may be based on the number of images considered by encoder 312 trained in FIG. 4A. Intelligent detector system 100 requires annotated ground truth map as part of training set 415 to train segmentation network 316. Intelligent detector system 100 may use loss function 413 represented as loss L(m, m') defining distance between the map m estimated by segmentation network 316 and ground truth map m'. Intelligent detector system 100 may compare between predicted map m and the ground truth map m' by using pixel-wise MSE and L1 loss functions and dice score and smooth dice score, for example.

In some embodiments, intelligent detector system 100 may use data augmentation, such as ad-hoc morphological operations and affine transformations with each image frame in input video and mask generated for each image frame, learning rate tuning, label smoothing, and/or batch training to improve results of segmentation network 316.

Figure 4D:
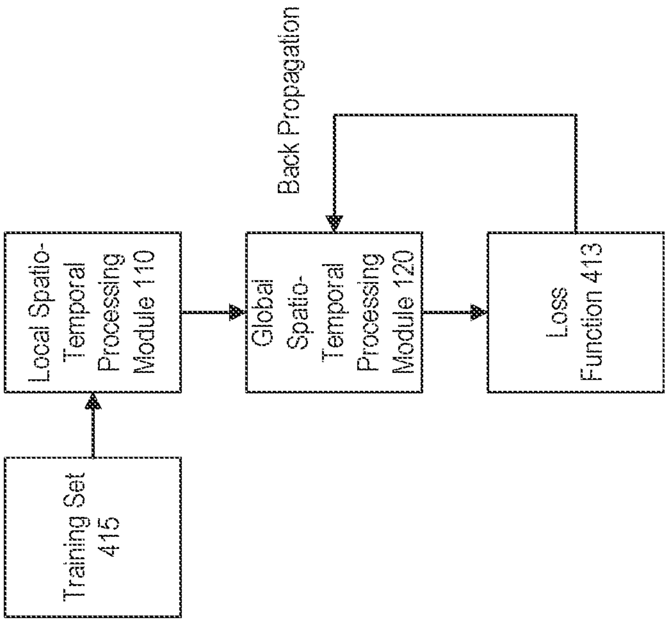
FIG. 4D is a flow diagram illustrating example training of the global spatio-temporal processing module of FIG. 3B, consistent with embodiments of the present disclosure.

FIG. 4D is a flow diagram illustrating example training of the global spatio-temporal processing module of FIG. 3B. The example training of FIG. 4D may be used for training global spatio-temporal processing module 120, consistent with embodiments of the present disclosure. As illustrated in FIG. 4D, intelligent detector system 100 may train global spatio-temporal processing module 110 by using the output of local spatio-temporal processing module 110. As will be appreciated from this disclosure, local spatio-temporal processing module 110 needs to be trained before using it in training global spatio-temporal processing module 120. Local spatio-temporal processing module 110 is trained by training individually each of its components as described in FIGS. 4A-4C description above.

Temporal convolution networks (TCNs) 321 of global spatio-temporal processing module 120 may access the whole timeseries of features T'×K extracted by local spatio-temporal processing module 110 working on T' image frames to generate feature vectors of 1×K dimension. Global spatio-temporal processing module 120 takes the whole matrix T'×K of features as input and returns a timeseries of scalar values of length T''. Intelligent detector system 100 may train global spatio-temporal processing module 120 by training TCNs 321.

Intelligent detector system 100 training of TCNs 321 and, in turn, global spatio-temporal processing module 120 may consider the number of processing layers of TCNs 321 and their architectural structure. The number of layers and connections vary based on task for determining features of interest and need to be tuned for each task.

Intelligent detector system 100 trains global spatio-temporal processing module 120 by computing K-dimensional timeseries of scores for image frames of each video in training set 415. Intelligent detector system 100 computes timeseries scores by providing training set 415 videos as input to previously trained local spatio-temporal processing module 110 and its output to global spatio-temporal processing module 120. Intelligent detector system 100 may use gradient-descent based optimization to estimate the network parameters of TCNs 321 neural network. Gradient-descent based optimization can minimize the distance between timeseries scores s output by global spatio-temporal processing module 120 and ground truth time series scores s'. Loss function 413 used to train global spatio-temporal processing module 120 can be a mean squared error (MSE), cross entropy, or Huber loss.

In some embodiments, intelligent detector system 100 may use data augmentation, learning rate tuning, label smoothing, and/or batch training techniques to improve results of trained global spatio-temporal processing module 120.

Figure 5A:
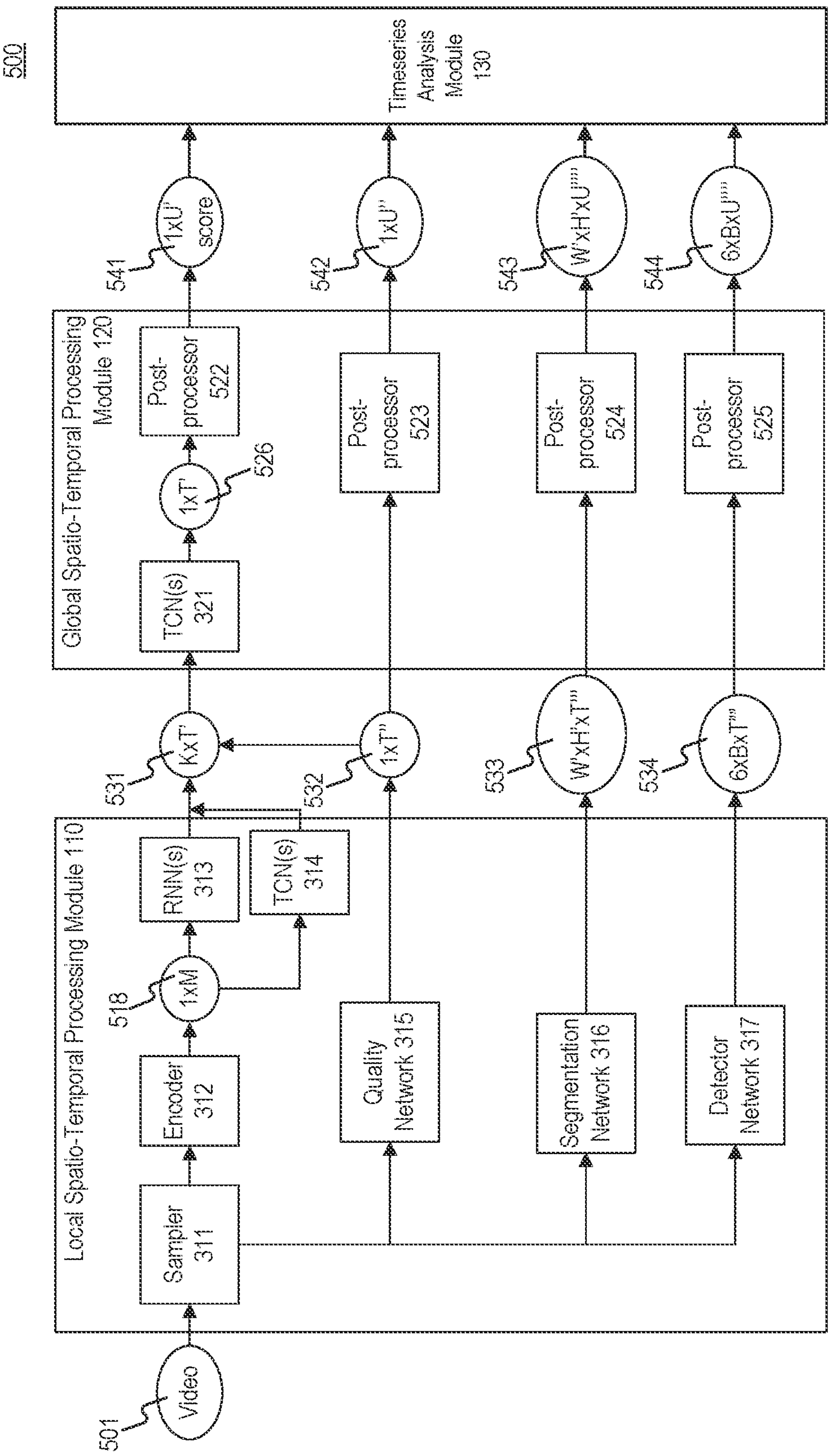
FIGS. 5A and 5B are schematic representations of pipelines constructed with components of an example intelligent detector system, consistent with embodiments of the present disclosure.
Figure 5B:
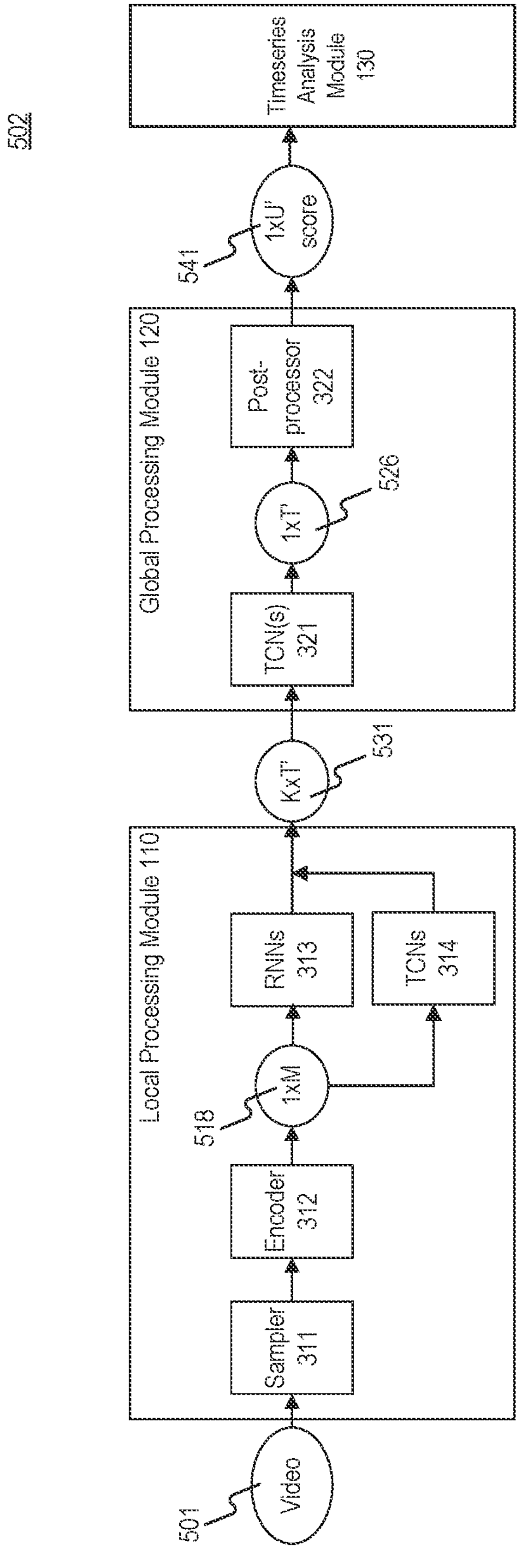

FIGS. 5A and 5B are schematic representations of pipelines constructed with components of an example intelligent detector system for processing input video or sets of images. By way of example, pipelines of FIGS. 5A and 5B may be constructed with the components of intelligent detector system 100 of FIG. 1A for processing input video. Pipelines to process input video using modules of intelligent detector system 100 can vary in structure based on the type of input video to process and requested features of interest. A pipeline may include all components or some components (e.g., encoder 312 of FIG. 3A) of each module.

As illustrated in FIG. 5A, pipeline 500 includes components of intelligent detector system 100 to process input video 501 and determine features of interest that may be requested by a user or physician (e.g., through user device 170 or physician device 180 of FIG. 1A). Pipeline 500 includes components of local spatio-temporal processing module 110 and global spatio-temporal processing module 120 to generate matrices 531 and 541 of scores of determined characteristics and requested features of interest in each image frame. Pipeline 500 also includes timeseries analysis module 130 to use spatio-temporal information of characteristics present in matrices 531 and 541 to determine the features of interest.

Local spatio-temporal processing module 110 may output a K×T' matrix 531 of characteristic scores. T' is the number of frames of input video 501 iteratively analyzed by local spatio-temporal processing module 110. Local spatio-temporal module 110 generates a vector of size K of characteristic scores for each analyzed frame of T' frames. The size K may match the number of features of interest requested by a user of intelligent detector system 100. Local spatio-temporal processing module 110 may process input video 501 using sampler 311 to retrieve some or all of the T image frames. T' frames, analyzed by the components of local spatio-temporal processing module to generate characteristic scores, can be less or equal to the total T image frames of input video 501. Sampler 311 may select T' frames for analysis by other components 312 and 315-317. In some embodiments, RNNs 313 and TCNs 314 may generate scores for only T' image frames of sampled frames. Networks 313-314 may include T' image frames based on the presence of at least one characteristic of the requested features of interest. Local spatio-temporal processing module uses only one set of networks 313 or 314 to process image frames and generate matrix 531 of characteristic scores.

Local spatio-temporal processing module generates the matrix 531 of characteristic scores for T' image frames by reviewing each image frame individually or in combination with a subset of image frames of input video 501 buffered and provided by sampler 311.

Local spatio-temporal processing module 110 may generate additional matrices 532-534 of scores using networks 315-317. Quality network 315 may generate a quality score of each image frame considered by sampler 311 for determining characteristics related to the features of interest in each image frame. As illustrated in FIG. 5A, quality network 315 may generate a matrix 532 of quality scores. Matrix 532 may be a 1×T" vector of quality scores of T" frames analyzed by quality network 315. Quality network 315 may analyze image frames extracted by sampler 311 to generate quality scores for T" image frames. In some embodiments, T" may be less than the total number of frames T of input video 501. Quality network 315 may only process T" frames with a quality score above a threshold value.

Segmentation network 316 may generate matrix 533 of segmentation masks by processing T'" image frames of input video 501. Matrix 533 is of dimensions W'×H'×T'" include T'" masks of height H' and width H'. In some embodiments, width W' and height H' of the segmentation mask may be lesser than the dimensions of a processed image frame. Segmentation network 316 may analyze image frames extracted by sampler 311 to generate segmentation masks for T'" image frames. In some embodiments, T'" may be less than the total number of frames T of input video 501. Segmentation network 316 may only process T" frames with a segmentation mask if they include at least some of the characteristics or requested features of interest.

As illustrated in FIG. 5A, global spatio-temporal processing module 120 processes the matrix 531 of K×T' scores of characteristics output by local spatio-temporal processing module 110 to produce revised matrix 541 of characteristics scores. Global spatio-temporal processing module 120 reviews characteristic scores of all analyzed T' image frames by processing matrix 531 of characteristics together. TCNs 321 in global spatio-temporal processing module 120 may process matrix 531 of characteristic scores to generate a matrix 526 of scores of dimension 1×T'. TCNs 321 generates matrix 526 of scores by combining score of T' image frames represented by a vector of size K. Global spatio-temporal processing module 120 may use post-processor 522 to remove any outliers in the matrix 526. Post-processor 522 may employ standard signal processing techniques such as low-pass filters and Gaussian smoothing to remove outliers. Global spatio-temporal processing module 120 outputs a matrix 541 of float scores of dimensions 1×U'. Dimension of U' may be less or equal to T'. Post-processor 522 may have filtered some of the T' image frame scores to generate refined matrix 541 of scores. In some embodiments, U' dimension may be greater than T' obtained by upsampling the input video to increase the number of image frames of the input video (e.g., video 501). Global spatio-temporal processing module 120 may include an upsampling module to increase the number of frames. Global spatio-temporal processing module 120 may upsample video 501 if the number of image frames with quality scores is lower than a threshold. Global spatio-temporal processing module 120 may upsample based on image frames with a high-quality score as determined by quality network 315 of local spatio-temporal processing module 110. In some embodiments, video 501 may be upsampled prior to processing by global spatio-temporal processing module 120. For example, sampler 311 may upsample input video 501 to create additional image frames.

Global spatio-temporal processing module 120 may use post-processors 523-525 to refine matrices 532-534 of additional scores and details used in determining requested features of interest to generate matrices 542-544.

By way of example, post-processor 523 refines quality scores matrix 532 using one or more standard signal processing techniques such as low-pass filters and Gaussian smoothing. Post-processor 523 outputs matrix 542 of dimension 1×U" of refined scores. In some embodiments, value U" may be different from value T". For example, U" may be less than T" if certain image frames of low quality score were ignored by post-processor 523. Alternatively, U" may be more than T" when video 501 is upsampled to generate more image frames and image frames with higher resolution.

Post-processor 524 may refine segmentation masks matrix 533 using a cascade of morphological operations exploiting prior information about the shape and distribution of each feature of interest. Post-processor 524 may output of matrix 543 of dimension W'×H'×U'". In some embodiments, the dimension of U'" may be different than T'". For example, U'" may be less than T'" if certain image frames of low quality score were ignored by post-processor 524. Alternatively, U'" may be more than T'" when video 501 is upsampled to generate more image frames and image frames with higher resolution.

As illustrated in FIG. 5A, timeseries module 130 of pipeline 500 may take output matrices 541-544 from global spatio-temporal processing module 120 to generate numerical values indicating a position in input video and location in each image frame of input video of the requested features of interest. Timeseries module 130 may use characteristic scores in matrix 541 and the quality scores matrix 542 to select the image frames that best represent the presence of each feature of interest. In some embodiments, timeseries module 130 may utilize spatio-temporal information of characteristics in image frames in matrix 541 to determine intervals in input video 501 that include the features of interest.

As illustrated in FIG. 5B, pipeline 502 showcases an alternative architecture, not including additional components such as networks 315-317 (as shown in FIG. 5A) and post-processors 523-525 (also shown in FIG. 5A). Pipeline 502 may still produce the same characteristic score matrices 531 and 541 as an output of local spatio-temporal processing module 110 and global spatio-temporal processing module 120. Timeseries module 130 takes the matrix 541 as input to produce the values identifying features of interest in input video 501.

Figure 6A:
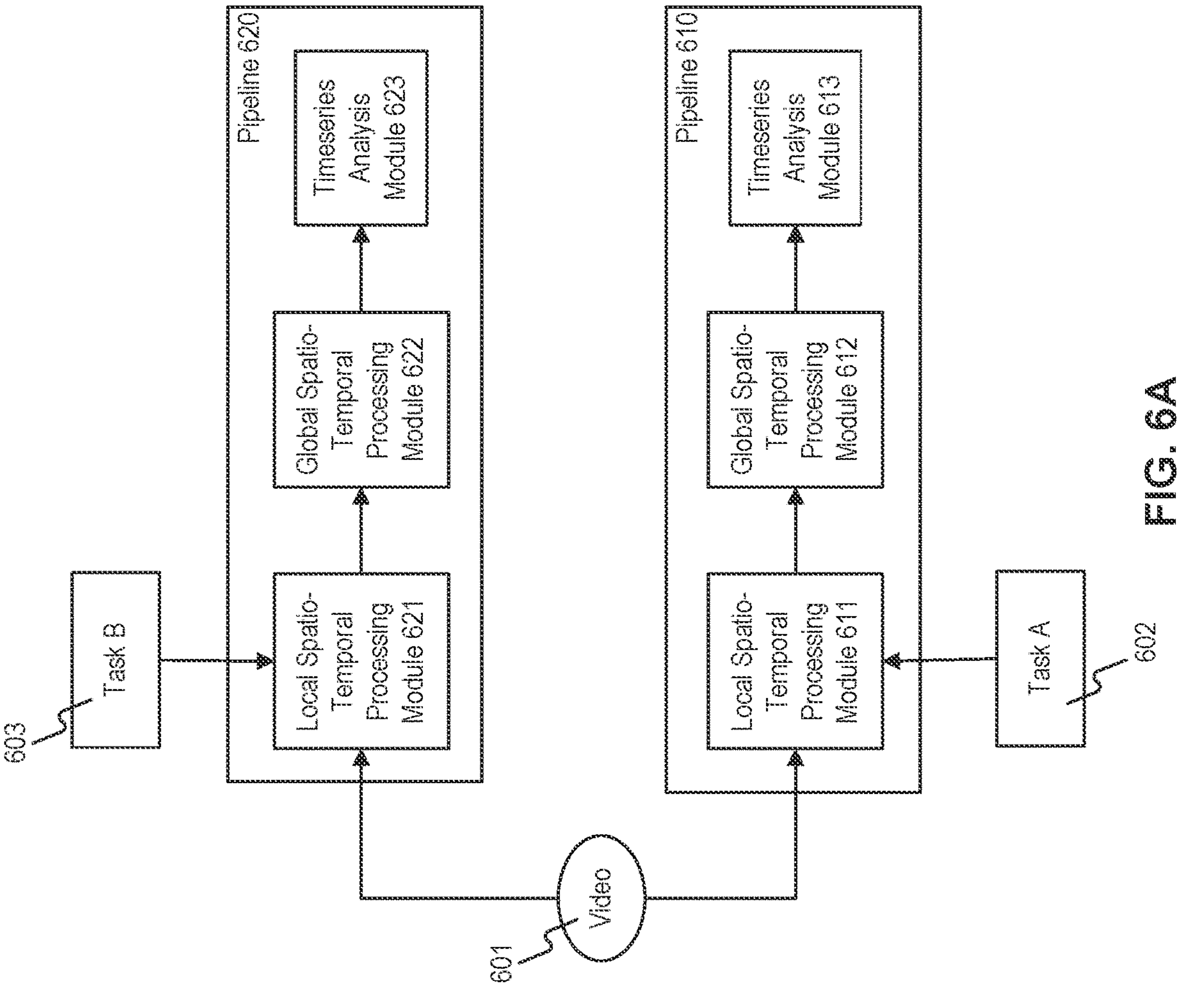
FIGS. 6A and 6B illustrate different pipeline setups for executing multiple tasks using an example intelligent detector system, consistent with embodiments of the present disclosure.
Figure 6B:
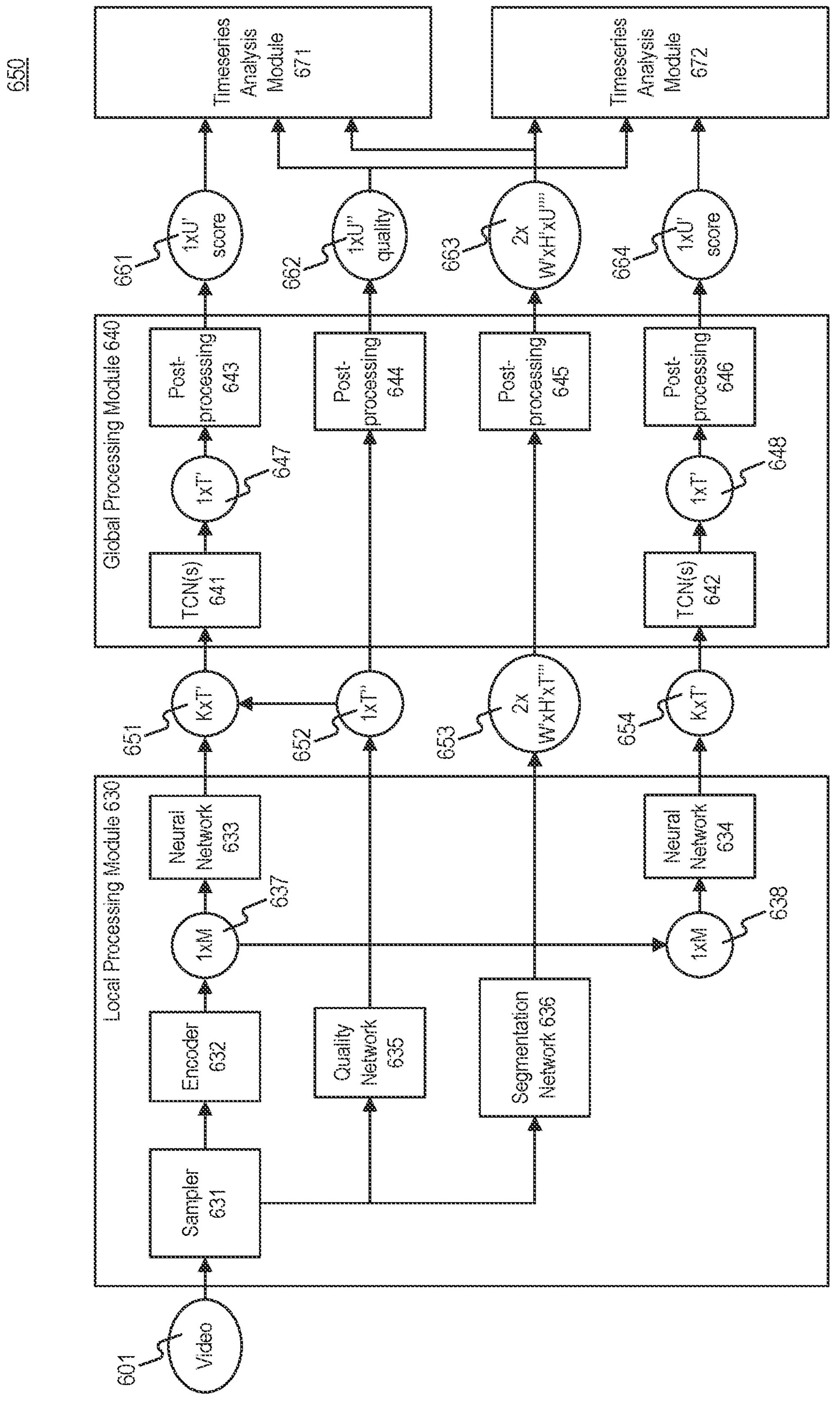

FIGS. 6A-6B illustrate different pipeline setups for executing multiple tasks using an intelligent detector system such as the example system 100 of FIG. 1A, consistent with embodiments of the present disclosure. The modules of intelligent detector system 100 may be configured and managed as a pipeline to process image data for different tasks. Task manager 140 may maintain different pipeline architectures and manage data flow across different modules in the pipeline. In some embodiments, intelligent detector system 100 may be utilized to determine various features of interest requested by different users from the same input video as different tasks. In such scenarios, neural networks in intelligent detector system 100 may be trained for different tasks to determine the features of interest relevant for each task. Intelligent detector system 100 may also be trained for different types of input video generated by different medical devices and/or other imaging devices to determine different features of interest.

Task manager 140 may maintain separate pipelines for each task and train them independently. As illustrated in FIG. 6A, Intelligent detector system 100 may use modules to generate two separate pipelines 610 and 620 and train them to work on separate tasks 602 and 603 to process input video 601 to detect different features of interest. In some embodiments, pipelines 610 and 630 are pre-trained to handle different tasks. Additionally, intelligent detector system 100 may instantiate a pipeline by retrieving the relevant pre-trained modules for processing input video 601. For example, task manager 140 may include local spatio-temporal module 611, global spatio-temporal module 612, and time series module 613 in pipeline 610 to process video 601 to determine features of interest requested as part of task 602. Similarly, pipeline 620 may be constructed using local spatio-temporal processing module 621, global spatio-temporal processing module 622, timeseries module 623 to process video 601 to determine features of interest as part of task 603. Maintenance of multiple pipelines helps easily extend to multiple tasks but may result in redundant processing of image data by certain components. An efficient alterative manner of a hybrid pipeline architecture with a partial set of shared components is described in the example FIG. 6B embodiment below.

FIG. 6B shows alternative pipeline 650 with shared modules of intelligent detector system 100 between tasks. Intelligent detector system 100 shares modules between different tasks by sharing some or all components of each module. Intelligent detector system 100 may share those components in a pipeline that are less dependent on requested tasks to process image data.

Sampler 311 and quality network 315 may rely on input image data and work on image data in the same manner irrespective of the requested features of interest. Accordingly, in pipeline 650, local spatio-temporal processing module 630's components sampler 631 and quality network 635 dependent on input data and unrelated to the requested task are shared between tasks 602 and 603 processing input video 601. Pipeline 650 can share their output between multiple tasks be processed by downstream components in pipeline 650.

Encoder 312 may depend on the requested task to identify the right annotations for image frames of input video 601, but it can depend more on the input data and can also be shared between different tasks. Accordingly, pipeline 650 may share encoder 632 among tasks 602 and 603. Further, sharing encoder 632 across tasks may improve its training due to the larger number of samples available across multiple tasks.

Quality network 315 directly works on the quality of the image without relying on the requested tasks. Thus, using separate instances of quality network 315, one per task becomes redundant as the quality score of an image frame in input video (e.g., input video 601) has no relation to the requested task (e.g., tasks 602 and 603) and will result in the same operation applied multiple times on input video 601.

Segmentation network 316 is more dependent on a requested task than the above-discussed components. However, it can still be shared as it is easier to generate multiple outputs for different tasks (e.g., tasks 602 and 603). As illustrated in FIG. 6B, segmentation network 636 is a modified version of segmentation network 316 that can return multiple segmentation masks per task for each image frame as matrix 653.

Neural networks 633-634 may include either instance of RNNs 313 or TCNs 314 that generate matrices of characteristics scores specific to requested features of interest to identify in different tasks. Local spatio-temporal processing module 630 of pipeline 650 may be configured to generate multiple copies of encoder output 637 and 638 and provided as input to multiple neural networks 633 and 634 one per task.

Figure 6C:
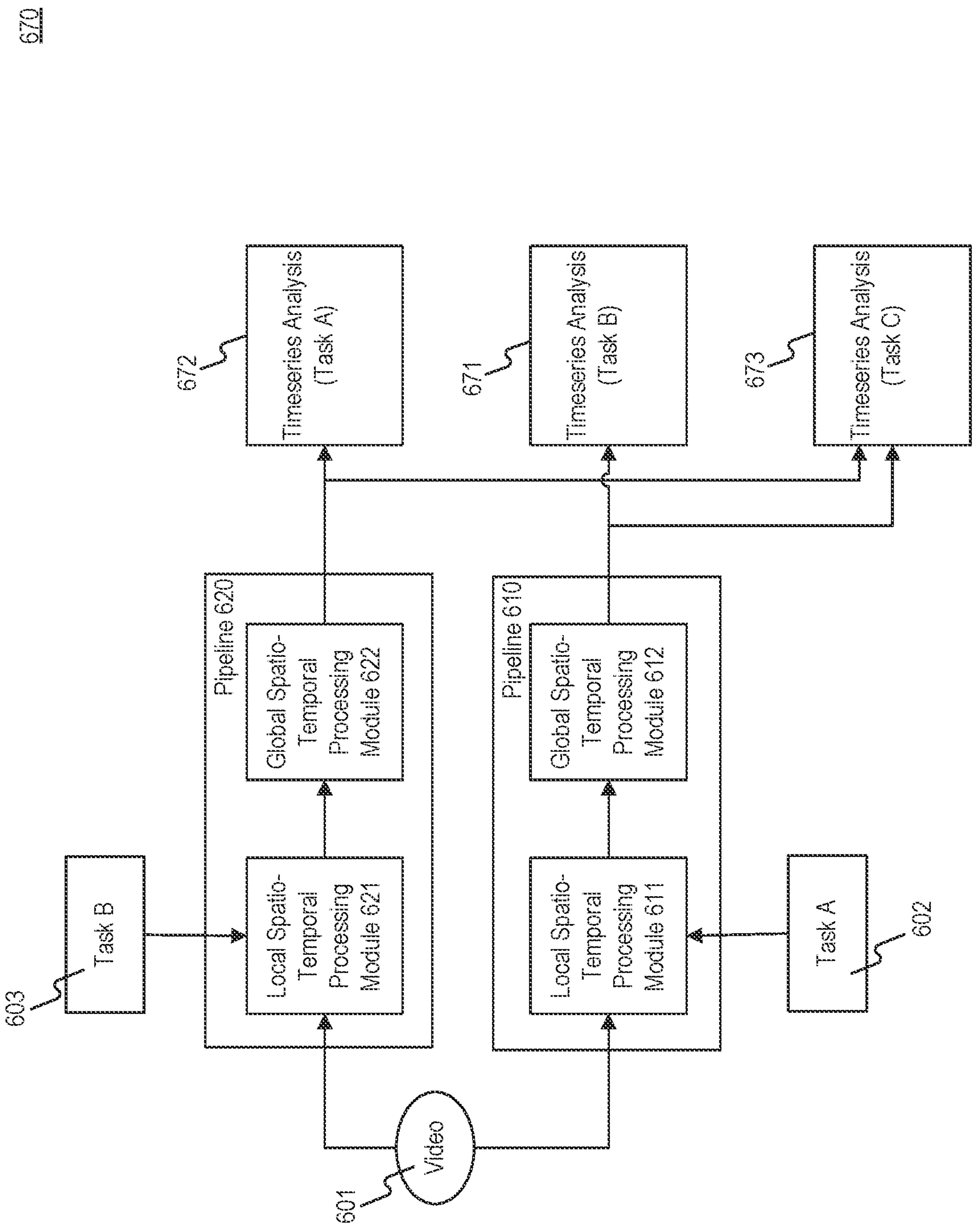
FIGS. 6C and 6D illustrate example pipeline setups for executing multiple tasks with aggregated output using an example intelligent detector system, consistent with embodiments of the present disclosure.
Figure 6D:
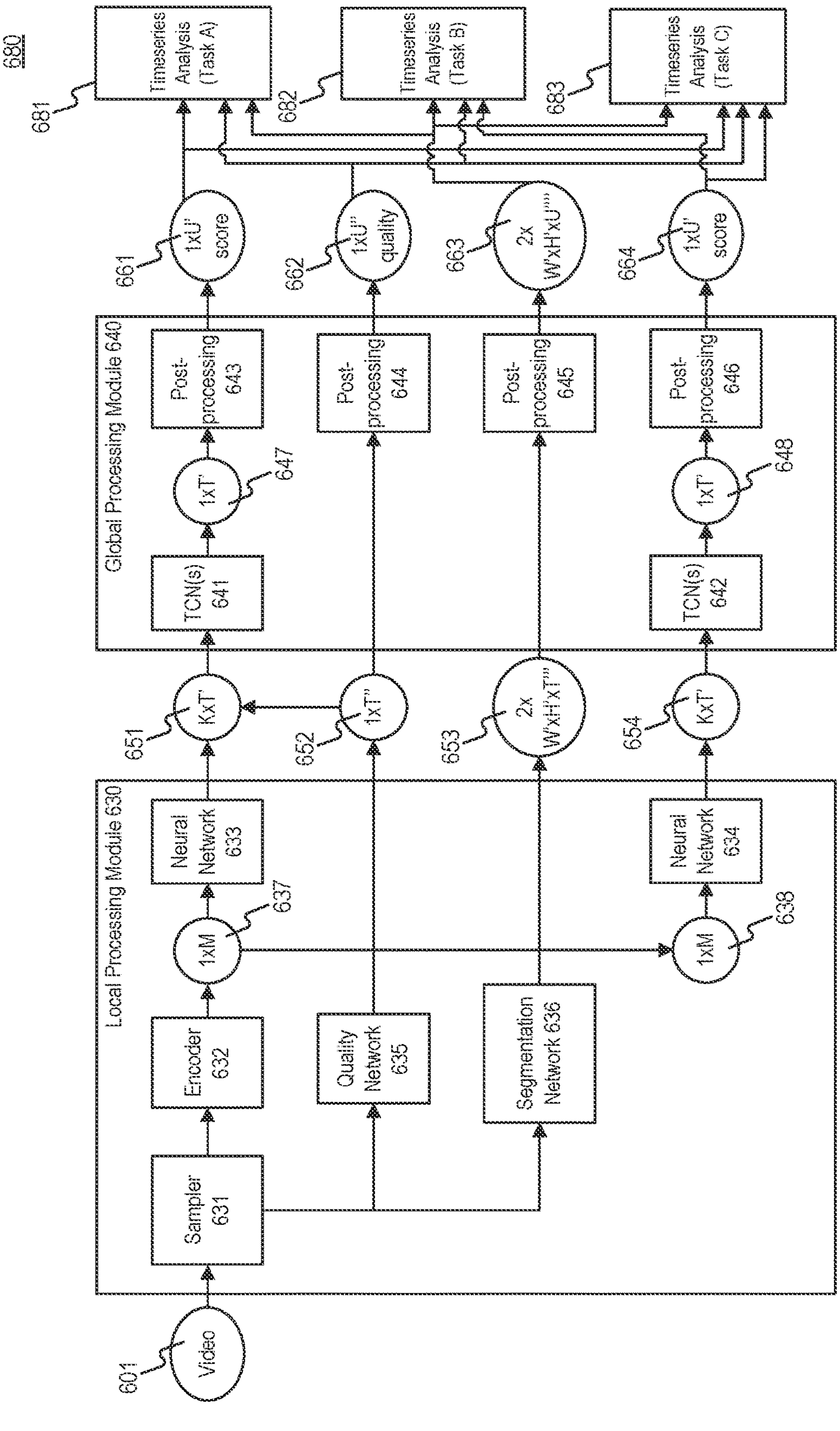

FIGS. 6C and 6D illustrate example pipeline setups for executing multiple tasks with aggregated output using an example intelligent detector system, consistent with embodiments of the present disclosure. As illustrated in FIG. 6C, pipelines 610 and 620 generate output by using multiple timeseries analysis modules 671-673 simultaneously. For example, timeseries analysis module 673 takes as input data generated by both pipelines 610 and 620. Timeseries analysis modules 671 and 672 may generate output of intelligent detector systems similar to outputs of pipelines 610 and 620 in FIG. 6A, described above. Additional timeseries analysis module 673 may aggregate the data generated by local and global spatio-temporal modules 611-612 and 621-622.

FIG. 6D illustrates pipelines sharing local and global spatio temporal modules 630 and 604 in additional to sharing the output of the modules to conduct timeseries analysis. As illustrated in FIG. 6D, timeseries analysis module 683 takes both vectors 661 and 664 including scores of images generated with and without pre-processing images using sampler 631 and encoder 632. Timeseries analysis module 683 aggregates the data to generate output similar to timeseries analysis module 673 in FIG. 6C.

Figure 6E:
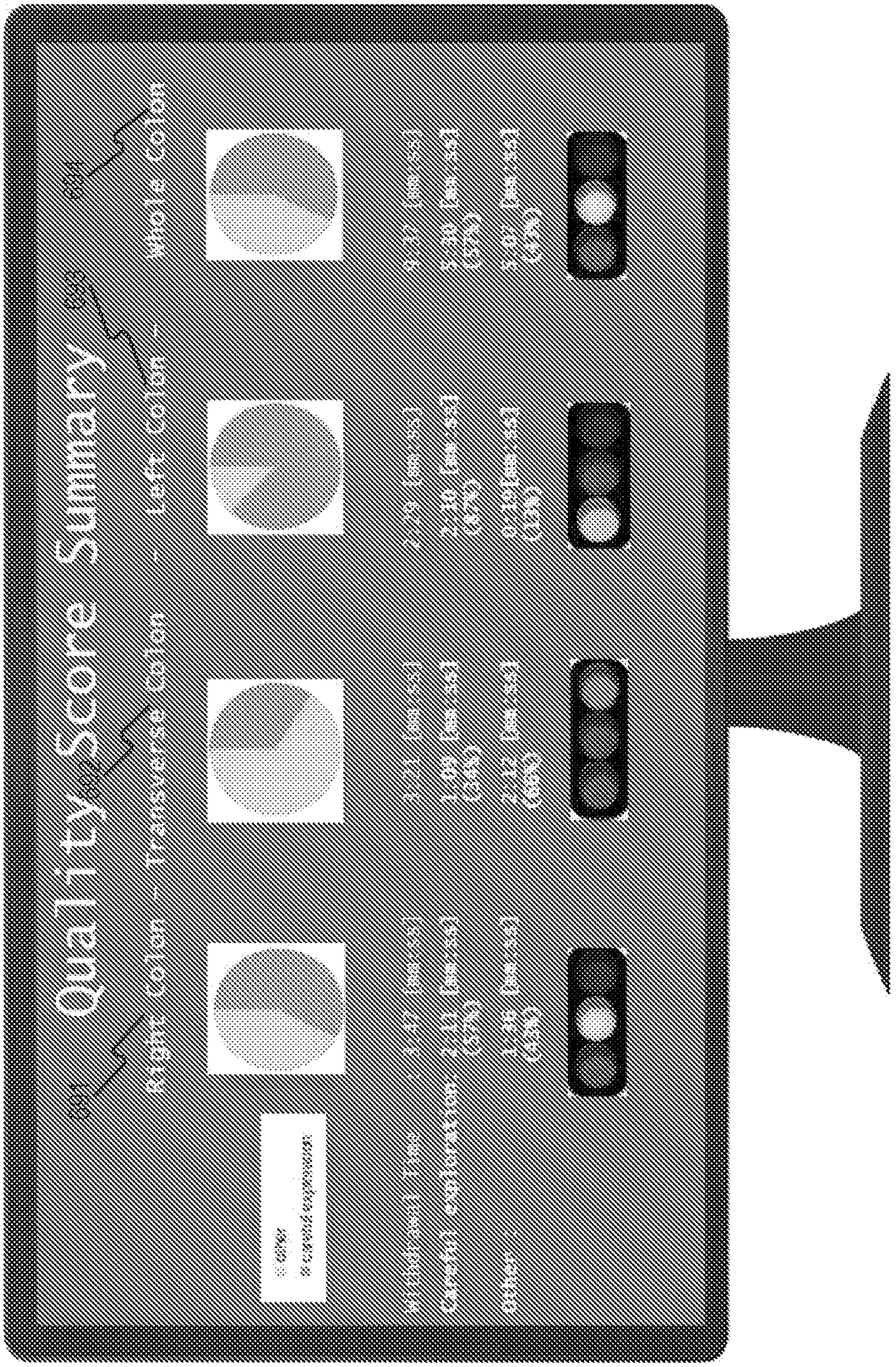
FIG. 6E illustrates an example dashboard with output summaries for multiple tasks generated using an example intelligent detector system, consistent with embodiments of the present disclosure.

FIG. 6E illustrates an example dashboard with output summaries for multiple tasks generated using an example intelligent detector system, consistent with embodiments of the present disclosure. Dashboard 690 may provide a summary of a medical procedure, for example, a colonoscopy performed by a healthcare professional. Dashboard 690 may provide information for different portions of the medical procedure and may also include scores and/or other information for summarizing the examination behavior of the healthcare professional behavior and identified features of interest, such as, the number of identified polyps.

As illustrated in FIG. 6E, dashboard 690 may include quality score summaries for different portions of the colon (right colon quality score summary 691, transverse colon quality score summary 692, and left colon quality score summary 693) along with a whole colon quality score summary 694. Quality score summaries 691-694 may include time statistics for different actions, such as careful exploration, performing a surgery, washing/cleaning the mucosa, and rapidly moving or navigating through the colon or other human organ. System 100 may determine, for example, the withdrawal time and the amount of time and/or percentage of time identified as a "careful exploration" based on characteristics or factors related to the healthcare professional's behavior. Intelligent detector system 100 may identify an action performed by a healthcare professional as a "careful exploration" based on, for example, the time spent by the healthcare professional analyzing a scanned portion of an organ versus other portions. For instance, an endoscopist analyzing the mucosa as opposed to other actions such as cleaning/resecting a lesion may be considered a "careful exploration" action. Time statistics may include summaries of other actions such as performing surgery, washing/cleaning an anatomical region or a portion of an organ (e.g., mucosa), and rapidly moving/navigating an anatomical location or organ during a medical procedure. Different medical procedures (e.g., colonoscopy, video surgery, video capsule-based scan) may include different actions of healthcare professionals as "careful exploration." Intelligent detector system 100 may be configured to label healthcare professionals' actions as "careful exploration." Quality score summary dashboard 690 may also include a color-coded representation of the quality of the examination for each portion of the medical procedure. For example, as illustrated in FIG. 6E, quality score summary dashboard 690 may include traffic light colored circles or icons (e.g., red, orange, and green) that are highlighted to indicate the quality level of the examination for each portion of the procedure.

Figure 7:
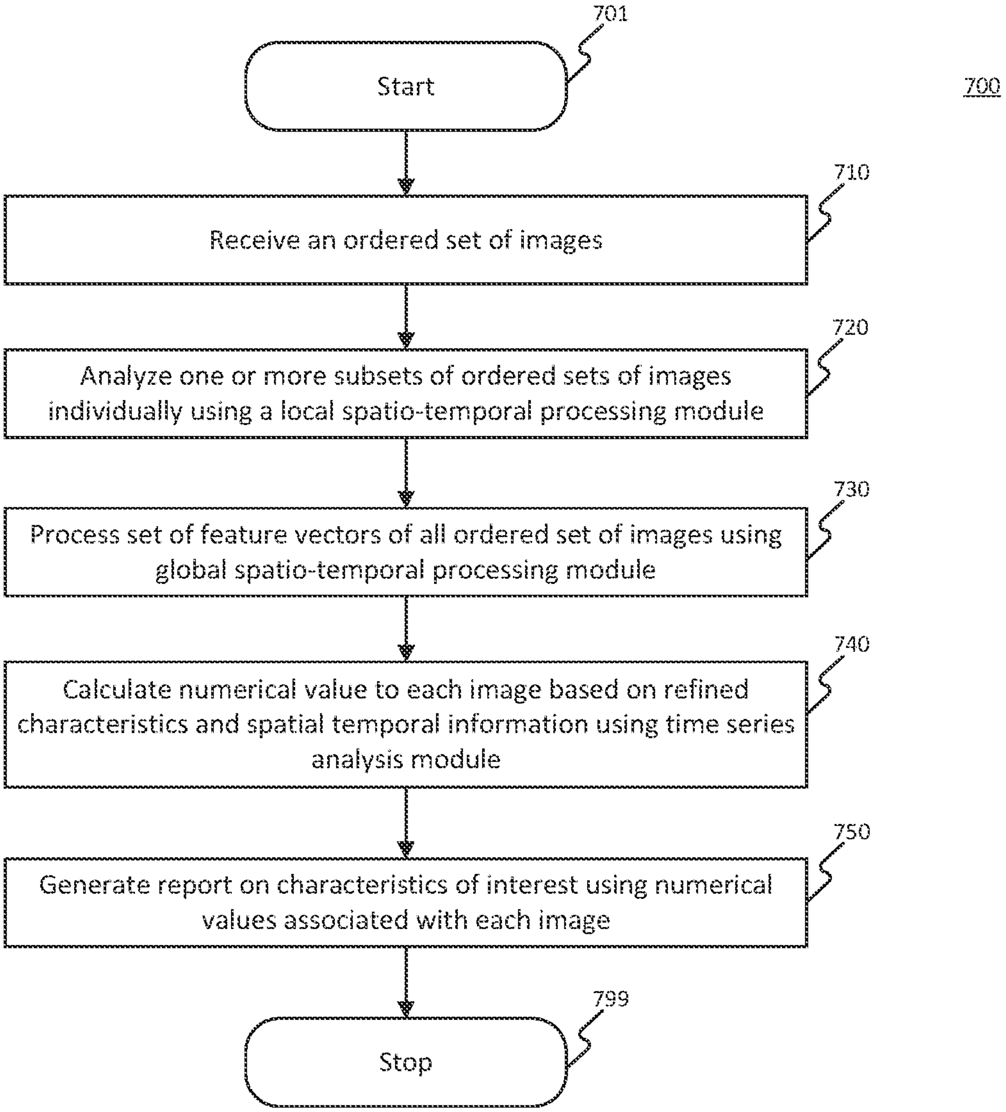
FIG. 7 is a flowchart depicting operations of an example method to analyze images and detect a feature of interest, consistent with embodiments of the present disclosure.

FIG. 7 is a flowchart depicting operations of an example method to detect pathology in input video of images, consistent with embodiments of the present disclosure. The steps of method 700 may be performed by intelligent detector system 100 of FIG. 1A executing on or otherwise using the features of computing device 200 of FIG. 2, for example. It will be appreciated that the illustrated method 700 may be altered to modify the order of steps and to include additional steps.

In step 710, intelligent detector system 100 may receive an input video or ordered set of images over network 160. As disclosed herein, the images to be processed may be temporally ordered. Intelligent detector system 100 may request images directly from image source 150. In some embodiments, other external devices such as physician device 180 and user device 170 may direct intelligent detector system 100 to request image source 150 for images. In some embodiments, user device 170 may submit a request to detect features of interest in images currently streamed or otherwise receive by image source 150.

In step 720, intelligent detector system 100 may analyze subsets of images individually to determine characteristics related to each requested feature of interest. Intelligent detector system 100 may use sampler 311 (as shown in FIG. 1A) to select a subset of images for analysis using other components of local spatio-temporal processing module 110 (as shown in FIG. 1A). Further, as disclosed herein, local spatio-temporal processing module 110 may have a limited subset of images when determining characteristics in an image.

Intelligent detector system 100 may allow configuration of the number of images to include in a subset of images, as disclosed herein. Intelligent detector system 110 may automatically configure the size of the subset based on the requested features of interest or characteristics related thereto. In some embodiments, a user of intelligent detector system 100 may configure the subset size based on input from a user or physician (e.g., through user device 170 or physician device 180 of FIG. 1A). The subsets of images may overlap and share images between them. Intelligent detector system 100 may allow configuration of the number of overlapping images between subsets of images processed by local spatio-temporal processing module 110. Intelligent detector system 100 may select a subset of images at once. In some embodiments, intelligent detector system 100 may receive a stream of images from image source 150 and may store them in a buffer until the required number of images to form a subset is achieved.

Intelligent detector system 100 may analyze the subset of images using local spatio-temporal processing module 110 to determine the likelihood of characteristics in each image of the subset of images. The likelihood of characteristics related to each feature of interest may be represented by a range of continuous or discrete values. For example, the likelihood of characteristics may be represented using a value ranging between 0 and 1.

Intelligent detector system 100 may detect characteristics by encoding each image of a subset of images using encoder 312. As part of the analysis process, intelligent detector system 100 may aggregate spatio-temporal information of the determined characteristics using recurrent neural network (E.g., RNN(s) 313 as shown in FIG. 3A). In some embodiments, intelligent detector system 100 may use causal temporal convolution network (e.g., TCN(s) 314 as shown in FIG. 3A) to extract spatio-temporal information of the determined characteristics in each image of a subset of images.

Intelligent detector system 100 may determine additional information about each image using quality network 315 (as shown in FIG. 3A). Intelligent detector system 100 may use quality network 315 to determine a vector of quality scores corresponding to each image of a subset of images. Quality scores may be used to rank each image relative to the ideal image with requested features of interest. Quality network 315 may output quality scores as an ordinal number. The ordinal numbers may be a range of numbers beyond which an image is too poor quality and needs to be ignored. For example, quality network 315 may output quality scores between 0 and R.

In some embodiments, Intelligent detector system 100 may generate additional information regarding characteristics using segmentation network 316. Additional information may include information on portions of images in each image. Intelligent detector system 100 may use segmentation network 316 to extract portions of the image with requested features of interest by generating segmentation masks for each image of a subset of images. Segmentation network 316 may use a deep convolution neural network to extract images.

In step 730, intelligent detector system 100 may process vectors of information about images and the determined characteristics of images in step 720. Intelligent detector system 100 may use global spatio-temporal processing module 120 to process output generated by local spatio-temporal processing module 110 in step 720. Intelligent detector system 100 may process vectors of information associated with all images together to refine vectors of information, including characteristics determined in each image. Global spatio-temporal processing module 120 may apply a non-causal temporal convolution network (e.g., Temporal Convolution Network(s) 321 of FIG. 3B) to refine the characteristic information generated by components of local spatio-temporal processing module 110.

Intelligent detector system 100 may also refine vectors with additional information about images and characteristics such as quality scores and segmentation masks using post-processors (e.g., post-processor 322 as shown in FIG. 3B). Intelligent detector system 100 may refine quality scores of each image of ordered set of images using one or more signal processing techniques. By way of example, intelligent detector system 100 may use one or more signal processing techniques such as low pass filters or Gaussian smoothing to refine the quality scores.

For example, as shown in FIG. 5A, post-processor 523 may take a quality score matrix 532 of quality scores to generate refined scores matrix 542.

In some embodiments, intelligent detector system 100 may refine segmentation masks used for image segmentation for extracting portions of each image containing requested features of interest using post-processors (e.g., post-processor 322 as shown in FIG. 3B). Intelligent detector system 100 may refine segmentation masks using morphological operations by exploiting prior information about the shape and distribution of characteristics or features of interest across an ordered set of images. For example, as shown in FIG. 5A, post-processor 524 may take a matrix of segmentation masks 533 as input to generate a refined matrix of segmentation masks 543.

In step 740, intelligent detector system 100 may associate numerical value to each image based on refined characteristics for each image of an ordered set of images in step 730. Components of intelligent detector system 100 may interpret the assigned numerical value of each image to determine the probability to identify a feature of interest within each image. Intelligent detector system 100 may present different numerical values to indicate different states of each requested feature of interest. For example, intelligent detector system 100 may output a first numerical value for each image where a requested feature of interests is detected and output a second numerical value for each image where the requested feature of interest is not detected.

In some embodiments, intelligent detector system 100 may interpret associated numerical value to determine a position in an image where a characteristic of a requested feature of interest is present or the number of images that include a characteristic. Following step 740, intelligent detector system 100 may generate a report (step 750) with information on each feature of interest based on the numerical values associated with each image. As disclosed above, the report may be presented electronically in different forms (e.g., a file, a display, a data transmission, and so on) and may include information about the presence of each requested feature of interest as well as additional information and/or recommendations based on, for example, medical guidelines. Intelligent detector system 100, upon completion of step 750, completes the process (step 799) and execution of method 700 on, for example, computing device 200.

Figure 8:
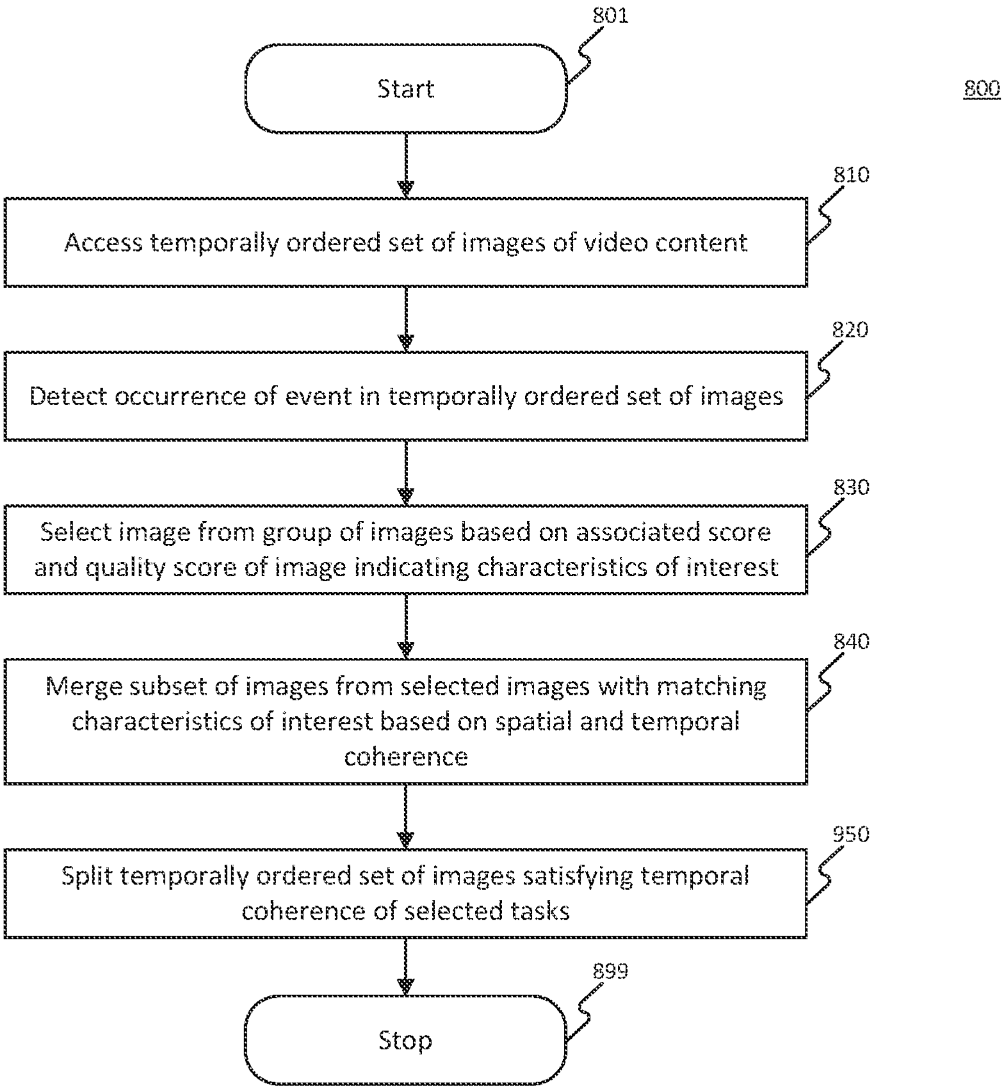
FIG. 8 is a flowchart depicting operations of an example method for spatio-temporal image analysis, consistent with embodiments of the present disclosure.

FIG. 8 is a flowchart depicting operations of an example method for spatio-temporal analysis of video content, consistent with embodiments of the present disclosure. The steps of method 800 may be performed by intelligent detector system 100 of FIG. 1A executing on or otherwise using the features of computing device 200 of FIG. 2, for example. It will be appreciated that the illustrated method 900 may be altered to modify the order of steps and to include additional steps.

In step 810, intelligent detector system 100 may access a temporally ordered set of images of video content over network 160 (as shown in FIG. 1A) from image source 150 (as shown in FIG. 1A). In some embodiments, intelligent detector system 100 may access images by extracting them from input video. In some embodiments, the received images may be stored and accessed from memory.

In step 820, intelligent detector system 100 may detect an occurrence of an event in the temporally ordered set of images using spatio-temporal information of characteristics in each image of the ordered set of images. Intelligent detector system 100 may detect events using event detector 331 (as shown in FIG. 3C). Intelligent detector system 100 may use local spatio-temporal processing module 110 and global spatio-temporal processing module 120 to determine spatio-temporal information. Intelligent detector system 100 may determine spatio-temporal information in a two-step manner. First, local spatio-temporal processing module may retrieve the spatio-temporal information about the characteristics by reviewing each image of the accessed set of images. In some embodiments, local spatio-temporal processing module 110 may use a subset of images. Second, global spatio-temporal processing module 120 may use the spatio-temporal information about characteristics local to each image to generate combined spatio-temporal information of all images by reviewing spatio-temporal information of all images generated by local spatio-temporal processing module 110.

Intelligent detector system 100 upon detection of an event may add color to a portion of a timeline of a video content that matches the subset of the temporally ordered set of images of the video content where an event was discovered.

The color may vary with the level of relevance of an image of a subset of a temporally ordered set of images for a characteristic related to a feature of interest. The color may vary with the level of relevance of an image of the subset of a temporally ordered set of images for one or more characteristics.

Intelligent detector system 100 may use the determined spatio-temporal information of characteristics to determine in a temporally ordered set of images where an event representing an occurrence of a feature of interest is present.

In step 830, intelligent detector system 100 may select an image from groups of images using frame selector 332 (as shown based on FIG. 2) based on the associated score and quality score of an image indicating the presence of characteristics related to at least one feature of interest. Intelligent detector system 100 may use quality network 335 to evaluate quality scores of each image of the images accessed in step 810. Frame selector 332 may review the images and use the quality scores generated by quality network 335 and characteristic scores generated in step 820 to determine the images with information. Intelligent detector system 100 may select image frames by adding bookmarks to images in the temporally ordered set of images.

In step 840, intelligent detector system 100 may merge subsets of images with matching characteristics based on spatial and temporal coherence using object descriptor 333. Intelligent detector system may determine spatial and temporal coherence of characteristics using spatio-temporal information of characteristics in each image determined in step 820.

In step 850, intelligent detector system 100 may split temporally ordered set of images satisfying temporal coherence of selected tasks using temporal segmentor 334 (as shown in FIG. 3C). Intelligent detector system 100 may split a set of images by identifying subsets with the presence of one or more features of interest. Intelligent detector system 100 may use the spatio-temporal information of characteristics determined in step 820 to determine temporal coherence. Intelligent detector system 100 may consider images to have temporal coherence if they have a matching presence of one or more features of interest.

Intelligent detector system 100 may extract a clip of the video content matching one of the split subsets of the temporally ordered set of images of the video. The extracted clips may include at least one feature of interest. Intelligent detector system 100, upon completion of step 850, completes (step 899) executing 800 on computing device 200.

Figure 9:
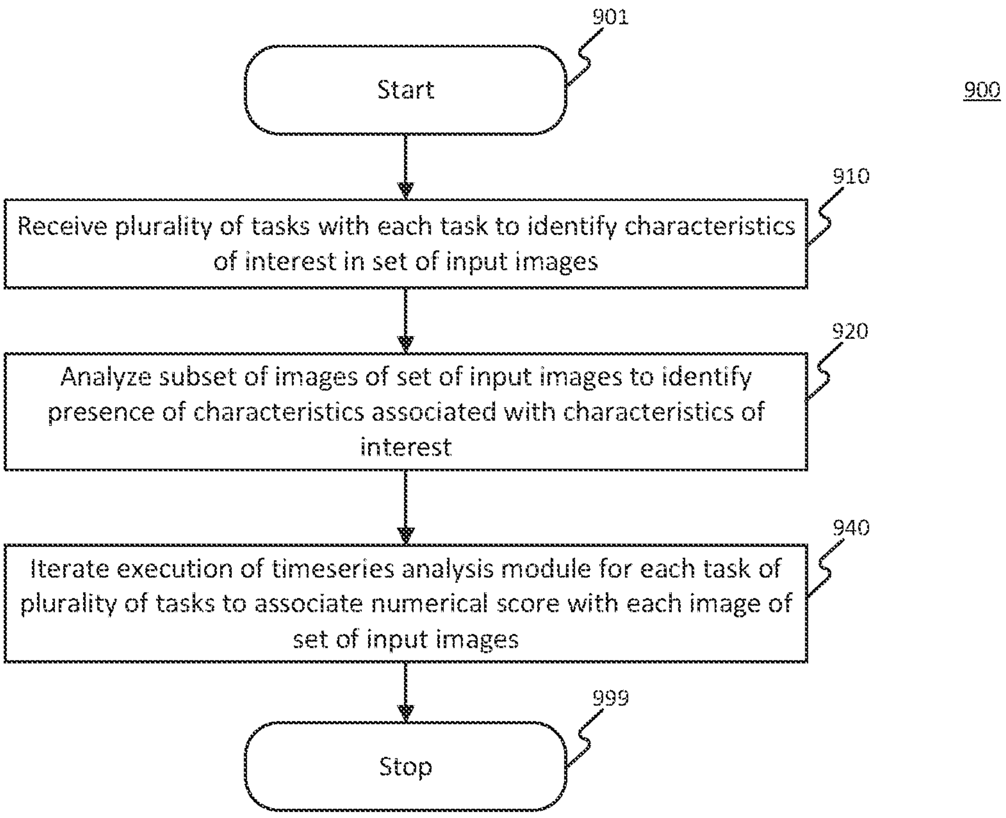
FIG. 9 is a flowchart depicting operations of an example method for processing a plurality of tasks on a set of input images, consistent with embodiments of the present disclosure.

FIG. 9 is a flowchart depicting operations of an example method 900 for a plurality of tasks on a set of input images, consistent with embodiments of the present disclosure. The steps of method 900 may be performed by intelligent detector system 100 of FIG. 1A executing on or otherwise using the features of computing device 200 of FIG. 2, for example. It will be appreciated that the illustrated method 900 may be altered to modify the order of steps and to include additional steps.

In step 910, intelligent detector system 100 may receive a plurality of tasks (e.g., tasks 602 and 603 of FIG. 6A) and an input video (e.g., input video 601 of FIG. 6A) including a set of images. Each of the received tasks 602 and 603 may include a request to identify features of interest in the set of input images in the input video.

In step 920, intelligent detector system 100 may analyze a subset of images using local spatio-temporal processing module 110 (as shown in FIG. 1A) to identify the presence of characteristics related to each requested feature of interest in each image of the subset of images.

In some embodiments, intelligent detector system 100 may use global spatio-temporal analysis module 120 to refine characteristics identified by local spatio-temporal processing module 110 by filtering incorrectly identified characteristics. In some embodiments, global spatio-temporal processing module 120 may highlight and flag some characteristics identified by local spatio-temporal processing module 110. In some embodiments, global spatio-temporal processing module 120 may filter using additional components such as quality network 315 and segmentation network 316 applied once against the set of images to generate additional information about the input images.

In step 930, intelligent detector system 100 may iteratively execute time series analysis module 130 for each task of the requested set of tasks to associate numerical score to each image of the input set of images. In some embodiments, intelligent detector system 100 may include multiple instances of timeseries module 130 to process multiple tasks simultaneously. For example, timeseries modules 671 and 672 (as shown in FIG. 6B) simultaneously identify different sets of characteristics in the same set of images for different tasks 602 and 603. Intelligent detector system 100, upon completion of step 930, completes (step 999) executing 900 on computing device 200.

The diagrams and components in the figures described above illustrate the architecture, functionality, and operation of possible implementations of systems, methods, and computer hardware or software products according to various example embodiments of the present disclosure. For example, each block in a flowchart or diagram may represent a module, segment, or portion of code, which includes one or more executable instructions for implementing the specified logical functions. It should also be understood that in some alternative implementations, functions indicated in a block may occur out of order noted in the figures. By way of example, two blocks or steps shown in succession may be executed or implemented substantially concurrently, or two blocks or steps may sometimes be executed in reverse order, depending upon the functionality involved. Furthermore, some blocks or steps may be omitted. It should also be understood that each block or step of the diagrams, and combination of the blocks or steps, may be implemented by special purpose hardware-based systems that perform the specified functions or acts, or by combinations of special purpose hardware and computer instructions. Computer program products (e.g., software or program instructions) may also be implemented based on the described embodiments and illustrated examples.

It should be appreciated that the above-described systems and methods may be varied in many ways and that different features may be combined in different ways. In particular, not all the features shown above in a particular embodiment or implementation are necessary in every embodiment or implementation. Further combinations of the above features and implementations are also considered to be within the scope of the herein disclosed embodiments or implementations.

While certain embodiments and features of implementations have been described and illustrated herein, modifications, substitutions, changes and equivalents will be apparent to those skilled in the art. It is, therefore, to be understood that the appended claims are intended to cover all such modifications and changes that fall within the scope of the disclosed embodiments and features of the illustrated implementations. It should also be understood that the herein described embodiments have been presented by way of example only, not limitation, and various changes in form and details may be made. Any portion of the systems and/or methods described herein may be implemented in any combination, except mutually exclusive combinations. By way of example, the implementations described herein can include various combinations and/or sub-combinations of the functions, components and/or features of the different embodiments described.

Moreover, while illustrative embodiments have been described herein, the scope of the present disclosure includes embodiments having equivalent elements, modifications, omissions, combinations (e.g., of aspects across various embodiments), adaptations or alterations based on the embodiments disclosed herein. Further, elements in the claims are to be interpreted broadly based on the language employed in the claims and not limited to examples described herein or during the prosecution of the present application. Instead, these examples are to be construed as non-exclusive. It is intended, therefore, that the specification and examples herein be considered as exemplary only, with a true scope and spirit being indicated by the following claims and their full scope of equivalents.

What is claimed is:

1. A system comprising:

one or more memory devices storing processor-executable instructions; and one or more processors configured to execute instructions to cause the system to perform operations for spatio-temporal analysis of images captured with an imaging device, the operations comprising:

access a temporally ordered set of images from the captured images;

detect, using an event detector, an occurrence of an event in the temporally ordered set of images, wherein a start time and an end time of the event are identified by a start image frame and an end image frame in the temporally ordered set of images;

select, using a frame selector, an image from a group of images in the temporally ordered set of images, bounded by the start image frame and the end image frame, based on an associated score and a quality score of the image, wherein the associated score of the selected image indicates a presence of at least one feature of interest;

merge a subset of images from the selected images based on a matching presence of the at least one feature of interest using an objects descriptor, wherein the subset of images is identified based on spatial and temporal coherence using spatio-temporal information; and split the temporally ordered set of images using temporal segmentor in temporal intervals which satisfy a temporal coherence of a selected task, wherein the selected task comprises a detection of the at least one feature of interest.

2. The system of claim 1, wherein the one or more processors are further configured to:

determine spatio-temporal information of characteristics related to the at least one feature of interest for subsets of images of video content using a local spatio-temporal processing module; and determine the spatio-temporal information of all images of the video content using a global spatio-temporal processing module.

3. The system of claim 1, wherein to split the temporally ordered set of images in temporal intervals, the one or more processors are further configured to:

identify a subset of temporally ordered set of images with the presence of the at least one feature of interest; or identify a subset of temporally ordered set of images with the presence of an event.

4. The system of claim 3, wherein to identify a subset of temporally ordered set of images with the presence of the at least one feature of interest, the one or more processors are further configured to:

add bookmarks to images in the temporally ordered set of images, wherein the bookmarked images are part of the subset of temporally ordered set of images.

5. The system of claim 3, wherein to identify a subset of temporally ordered set of images with the presence of the at least one feature of interest, the one or more processors are further configured to:

extract a set of images from the subset of the temporally ordered set of images.

6. The system of claim 5, wherein the extracted set of images includes characteristics related to the at least one feature of interest.

7. The system of claim 3, wherein to identify a subset of temporally ordered set of images with the presence of the at least one feature of interest, the one or more processors are further configured to:

add color to a portion of a timeline of the captured images that matches the subset of the temporally ordered set of images.

8. The system of claim 7, wherein the color varies with a level of relevance of an image of the subset of temporally ordered set of images for the at least one feature of interest.

9. The system of claim 7, wherein the color varies with a level of relevance of an image of the subset of temporally ordered set of images for characteristics related to the at least one feature of interest.

10. The system of claim 7, wherein the color differs with different features of interest related to the at least one feature of interest.

11. The system of claim 7, wherein the color differs with different events detected using the event detector.

12. The system of claim 8, wherein the timeline is presented as part of a video summary, wherein the video summary includes overlaid text and graphics.

13. The system of claim 12, wherein the video summary is generated by selecting relevant frames from the captured images and has a variable frame rate video output.

14. The system of claim 1, wherein the occurrence of the event represents a portion of a medical procedure.

15. The system of claim 1, wherein the one or more processors are further configured to:

generate a dashboard with summary of the temporally ordered set of images, wherein the summary includes images selected using a frame selector module and augmented with display markings.

16. The system of claim 15, wherein the generated dashboard includes quality scores of a medical procedure performed while images are captured using the imaging device.

17. The system of claim 15, wherein the generated dashboard includes quality scores of an operator of the imaging device performing a medical procedure.

18. The system of claim 15, wherein the generated dashboard comprises aggregated information from one or more of the event detector, frame selector, object descriptor, and temporal segmentor.

19. The system of claim 1, wherein the ordered set of images are received directly from the imaging device during a medical procedure.

20. The system of claim 1, wherein the presence of at least one feature of interest is determined from a portion of the captured images.

21. The system of claim 1, wherein the one or more processors are further configured to:

receive a plurality of tasks, wherein at least one task of the plurality of tasks is associated with a request to identify at least one feature of interest in the set of images;

analyze, using a local spatio-temporal processing module, a subset of images of the set of images to identify the presence of characteristics associated with the at least one feature of interest; and iterate execution of a timeseries analysis module for each task of the plurality of tasks to associate a numerical score for each task with each image of the subset of images.

22. The system of claim 21, wherein the local spatio-temporal processing module outputs subsets of analyzed images of the set of images, wherein each subset is associated with a task of the plurality of tasks.

23. The system of claim 21, wherein the local spatio-temporal processing module determines the presence of characteristics by determining a vector of quality scores, wherein each quality score in the vector of quality scores corresponds to each image of the subset of the images.

24. The system of claim 21, wherein the local spatio-temporal processing module generates a set of feature vectors for features of interest related to the plurality of tasks.

25. The system of claim 21, wherein the one or more processors are further configured to:

analyze, using a global spatio-temporal processing module, sets of feature vectors for the subset of images analyzed by the local spatio-temporal processing module.

26. The system of claim 21, wherein the one or more processors are further configured to:

aggregate output of the local spatio-temporal processing module for each task of the plurality of tasks using the timeseries analysis module.

27. A method for spatio-temporal analysis of images captured with an imaging device, the method comprising:

accessing a temporally ordered set of images from the captured images;

detecting, using an event detector, an occurrence of an event in the temporally ordered set of images, wherein a start time and an end time of the event are identified by a start image frame and an end image frame in the temporally ordered set of images;

selecting, using a frame selector, an image from a group of images in the temporally ordered set of images, bounded by the start image frame and the end image frame, based on an associated score and a quality score of the image, wherein the associated score of the selected image indicates a presence of at least one feature of interest;

merging a subset of images from the selected images based on a matching presence of the at least one feature of interest using an objects descriptor, wherein the subset of images are identified based on spatial and temporal coherence using spatio-temporal information generated by a local spatio-temporal processing module; and splitting the temporally ordered set of images using temporal segmentor in temporal intervals which satisfy a temporal coherence of a selected task, wherein the selected task comprises a detection of the at least one feature of interest.

28. A non-transitory computer readable medium including instructions that when executed by at least one processor, cause the at least one processor to perform operations for spatio-temporal analysis of images captured with an imaging device, the operations comprising:

accessing a temporally ordered set of images from the captured images;

detecting, using an event detector, an occurrence of an event in the temporally ordered set of images, wherein a start time and an end time of the event are identified by a start image frame and an end image frame in the temporally ordered set of images;

selecting, using a frame selector, an image from a group of images in the temporally ordered set of images, bounded by the start image frame and the end image frame, based on an associated score and a quality score of the image, wherein the associated score of the selected image indicates a presence of at least one feature of interest;

merging a subset of images from the selected images based on a matching presence of the at least one feature of interest using an objects descriptor, wherein the subset of images are identified based on spatial and temporal coherence using spatio-temporal information generated by a local spatio-temporal processing module; and splitting the temporally ordered set of images using temporal segmentor in temporal intervals which satisfy a temporal coherence of a selected task, wherein the selected task comprises a detection of the at least one feature of interest.

* * * * *